US008277799B2

(12) United States Patent
Farmer

(10) Patent No.: US 8,277,799 B2
(45) Date of Patent: *Oct. 2, 2012

(54) INHIBITION OF PATHOGENS BY PROBIOTIC BACTERIA

(75) Inventor: Sean Farmer, Miami Beach, FL (US)

(73) Assignee: Ganeden Biotech, Incorporated, Mayfield Heights, OH (US)

( * ) Notice: Subject to any disclaimer, the term of this patent is extended or adjusted under 35 U.S.C. 154(b) by 126 days.

This patent is subject to a terminal disclaimer.

(21) Appl. No.: 12/756,658

(22) Filed: Apr. 8, 2010

(65) Prior Publication Data
US 2011/0189145 A1 Aug. 4, 2011

Related U.S. Application Data

(60) Division of application No. 11/706,642, filed on Feb. 13, 2007, now Pat. No. 7,713,726, which is a continuation of application No. 11/005,897, filed on Dec. 16, 2004, now abandoned, which is a continuation of application No. 09/708,870, filed on Nov. 8, 2000, now Pat. No. 6,849,256.

(60) Provisional application No. 60/163,959, filed on Nov. 8, 1999, provisional application No. 60/198,404, filed on Apr. 19, 2000.

(51) Int. Cl.
*A01N 63/00* (2006.01)
*C12N 1/20* (2006.01)

(52) U.S. Cl. .............. 424/93.46; 435/252.31; 435/832

(58) Field of Classification Search .................. None
See application file for complete search history.

(56) References Cited

U.S. PATENT DOCUMENTS

| | | |
|---|---|---|
| 4,110,477 A | 8/1978 | Naruse et al. |
| 4,210,672 A | 7/1980 | Hata |
| 4,323,651 A | 4/1982 | Long et al. |
| 4,980,180 A | 12/1990 | Cully et al. |
| 5,079,164 A | 1/1992 | Kirkovits et al. |
| 5,102,800 A | 4/1992 | Hirikoshi |
| 5,176,911 A | 1/1993 | Tosi et al. |
| 5,200,336 A | 4/1993 | Kong et al. |
| 5,413,960 A | 5/1995 | Dobrogosz et al. |
| 5,439,678 A | 8/1995 | Dobrogosz et al. |
| 5,439,995 A | 8/1995 | Bailly et al. |
| 5,968,569 A | 10/1999 | Cavadini et al. |
| 6,165,775 A | 12/2000 | Shigemitsu |
| 6,461,607 B1 | 10/2002 | Farmer |
| 6,849,256 B1 * | 2/2005 | Farmer .................. 424/93.46 |
| 7,700,093 B2 * | 4/2010 | Farmer et al. .......... 424/93.46 |
| 7,713,726 B2 | 5/2010 | Farmer |
| 7,767,203 B2 * | 8/2010 | Farmer et al. .......... 424/93.46 |
| 7,854,927 B2 * | 12/2010 | Farmer et al. .......... 424/93.46 |
| 2005/0232909 A1 | 10/2005 | Farmer |

FOREIGN PATENT DOCUMENTS

| | | |
|---|---|---|
| EP | 0862863 A2 | 9/1998 |
| JP | 7298833 A | 11/1995 |
| JP | 9194384 A | 7/1997 |
| WO | WO-93/14187 A1 | 7/1993 |
| WO | WO-94/11492 A1 | 5/1994 |
| WO | WO-9702757 A1 | 1/1997 |
| WO | WO-98/47374 A1 | 10/1998 |
| WO | WO-98/54982 A1 | 12/1998 |
| WO | WO-9949877 A2 | 10/1999 |
| WO | WO-00/07606 A2 | 2/2000 |
| WO | WO-00/10582 A2 | 3/2000 |
| WO | WO-00/61201 A1 | 10/2000 |
| WO | WO-01/13927 A2 | 3/2001 |
| WO | WO-01/13956 A2 | 3/2001 |
| WO | WO-01/34168 A1 | 5/2001 |

OTHER PUBLICATIONS

Arthur et al. *Antimicrob. Agents Chemother.*, 37(8)1563-1571 (1993).
*ATCC Catalogue of Bacteria and Bacteriophages*, Accession No. 11014, (1996).
*ATCC Catalogue of Bacteria and Bacteriophages*, Accession No. 11369, (1996).
*ATCC Catalogue of Bacteria and Bacteriophages*, Accession No. 15949, (1996).
*ATCC Catalogue of Bacteria and Bacteriophages*, Accession No. 31284, (1996).
Baker at al. *Can. J. Microbiol.*, 6:557-563 (1960).
Banerjee et al. *Arch. Intern. Med.*, Abstract XP000982042, 148:1769-1774 (1988).
Barefoot et al. *J. Dairy Sci.*, 76:2366-2379 (1993).
Bergey's Manual of Systematic Bacteriology, 2:1128, 1131 (1984).
Bernet et al. *Applied Environ. Microbiol.*, 59(12):4121-4128 (1993).
Bernet et al. *Gut*, 35(4):483-489 (1994).
Blum et al. *Electrophoresis*, 8(1):93-99 (1987).
Bush et al. *Ann. Intern. Med.*, 110(7):515-520 (1989).
Challa et al. *Carcinogenesis*, 18(3):517-521 (1997).
Christi et al. *Gut*, 33(9):1234-1238 (1992).
Clark et al. *Antimicrob. Agents Chemother.*, 37(11):2311-2317 (1993).
Clewell D. B. *Annu. Rev. Microbiol.*, 40:635-659 (1986).
Clewell D. B. *Microbiol. Rev.*, 45(3):409-436 (1981).
Clewell at al. *Plasmid*, 21(3):175-184 (1989).
De Simone et al. *Immunopharmacol. Immunotoxicol.*, 14(1&2):331-340 (1992).
Devriese et al. *J. Appl. Bacteriol.*, 75:399-408 (1993).
DSM No. 2356, *Bacillus coagulans* Hammer 1915 emend. De Clerck et al., 2004 (NCIB 8523).
DSM No. 2383, *Bacillus coagulans* Hammer 1915 emend. De Clerck et al., 2004 (ATCC 11014).
DSM No. 2384, *Bacillus coagulans* Hammer 1915 emend. De Clerck et al., 2004 (ATCC 11369).
DSM No. 2385, *Bacillus coagulans* Hammer 1915 emend. De Clerck et al., 2004 (ATCC 15949).

(Continued)

*Primary Examiner* — Vera Afremova
(74) *Attorney, Agent, or Firm* — Mintz Levin Cohn Ferris Glovsky and Popeo, P.C.; Ingrid A. Beattie

(57) ABSTRACT

Compositions containing a lactic acid-producing bacterial strain, e.g., *Bacillus coagulans* for inhibition of pathogenic bacterial infections. Spores or extracellular products produced by the bacterial strains are also useful as inhibitory agents.

11 Claims, 12 Drawing Sheets

OTHER PUBLICATIONS

Eliopoulos et al. *Antimicrob. Agents Chemother.*, 38(3):534-541 (1994).
Elmer et al. *JAMA*, 275(11):870-876 (1996).
Famularo et al., "Stimulation of Immunity by Probiotics", in *Probiotics 2: Applications and practical aspects*, Fuller, R., Ed., Chapman and Hall, London, Ch. 6, pp. 133-161 (1997).
Fuller R. *J. Applied Bacteriol.*, 66:365-378 (1989).
Gandi, A.B., "*Lactobacillus sporogenes*: An Advancement in *Lactobacillus* Therapy", *Townsend Lett. Doctors & Patients*, 150:108-110 (1994).
Gibson et al. *Gastroenterol.*, 108(4):975-982 (1995).
Gorbach S. L. *Annals Med.*, 22(1):37-41 (1990).
Hiramatsu et al. *J. Antimicrob. Chemother.*, 40(1):135-136 (1997).
Horodniceanu et al. *Antimicrob. Agents Chemother.*, 16(5):686-689 (1979).
Hughes et al. *Abst. Pres. Ann. Meeting Am. Phytop. Soc.*, 78:1502-1503 (1988).
Hughes et al. *Anal. Chem.*, 61:1656-1660 (1989).
Hyronimus et al. *Int. J. Food Microbial.*, Abstract XP000982058, 61:193-197 (2000).
Kim et al. *Yakhak Hoeji (J. Pharm. Soc. Korea)*, English abstract XP000986457, 41(4):450-455 (1997).
Klaenhammer et al. *FEMS Microbiol. Rev.*, 12:39-85 (1993).
Koo et al., "Long-Term Effect of *Bifidobacteria* and Neosugar on Precursor Lesions of Colonic Cancer in $CF_1$ Mice", *Nutrit. Cancer*, 16:249-257 (1991).
Laemmli, U.K., "Cleavage of Structural Proteins during the Assembly of the Head of Bacteriophage T4", *Nature*, 227:680-685 (1970).
Lidbeck et al. *Eur. J. Cancer Prev.*, 1(5):341-353 (1992).
Malin et al. *Ann. Nutr. Metab.*, 40(1):137-145 (1996).
Matsumura et al. *Animal Sci. Technol. (Jpn)*, 63:1157-1159 (1992).
Metchnikoff, E., "Longevity in the Animal Kingdom" in *The Prolongation of Life Optimistic Studies*, G.P. Putnam's Sons, Eds., New York, pp. 39-183 (1910).
Mitchell P. *The Lancet*, 352(9126):462-463 (1998).
Montecalvo et al. *Antimicrobiol. Agents Chemother.*, 38:1363-1367 (1994).
Mossman et al. *Appl. Spectroscopy*, 51:1443-1446 (1997).
Nakamura et al. *Int. J. Syst. Bacteriol.*, 38(1):63-73 (1988).
Noble et al. *FEMS Microbiol. Lett.*, 93:195-198 (1992).
Palop et al. *Applied Environ. Microbiol.*, Abstract XP000982089, 63(6):2246-2251 (1997).
Perdigon et al. *J. Dairy Sci.*, 78:1597-1606 (1995).
Quale et al. *Clin. Infect. Dis.*, 23(5):1020-1025 (1996).
Rafter J. J. *Scand. J.Gastroenterol.*, 30:497-502 (1995).
Reddy et 81. *Cancer Res.*, 53(17):3914-3918 (1993).
Reid et al. *Clin. Microbiol. Rev.*, 3(4):335-344 (1990).
Rice et al. *Applied Environ. Microbiol.*, 61(1):374-376 (1995).
Roberts M. C. *Antimicrob. Agents Chemother.*, 34(3):476-478 (1990).
Rowland et al. *Applied Microbiol.*, 29(1):7-12 (1975).
Saavedra et al. *The Lancet*, 344(8929):1046-1049 (1994).
Sahm eat al. *Antimicrob. Agents Chemother.*, 33(9):1588-1591 (1989).
Saitou et al. *Mol. Biol. Evol.*, 4:406-425 (1987).
Salminen et at. *Antonio van Leeuwenhoek*, 70(2-4):347-358 (1996).
Sapico et al. *J. Clin. Microbiol.*, 27(9):2091-2095 (1989).
Schiffrin et al., "Immune modulation of blood leukocytes in humans by lactic acid bacteria: criteria for strain selection", *Am. J. Clin. Nutr.*, 66(Suppl):5S-20S (1997).
Sekine et al. *Bifidobacteria and Microflora*, 13:65-77 (1994).
Shannon et al., "Multiple-antibiotic-resistant *salmonella*", *Lancet*, 352:490-491 (1998).
Sneath P. H. A. *Bergey's Manual of Systematic Bacteriology*, 2:1104, 1117, (1986).
Sneath P. H. A. *Bergey's Manual of Systematic Bacteriology*, 2:1128, (1986).
Solis-Pereyra et al. *Nutr.Res.*, 13(10):1127-1140 (1993).
Stackebrandt et al. *Int. J. Syst. Bactetiol.*, 44(4):846-849 (1994).
Standiford et al. *Infect. Immun.*, 62(1):119-125 (1994).
Tojo et al. *Acta Pediatr. Jpn.*, 29:160-167 (1987).
Waterman, M.S., "Introduction to Computational Biology, Maps, sequences and genomes", Chapman and Hall Publishing, Boca Raton, pp. 360-365 (1995).
Winberg et al. *Pediatr. Nephrol.*, 7(5):509-514 (1993).
Yamazaki et al. *Bifidobacteria and Microflora*, 1:55-59 (1982).
Yanagida et al. *J. Gen. Appl. Microbiol.*, 33:33-45 (1987).
Zervos et al. *Ann. Intern. Med.*, 106:887-691 (1987).
Zhang et al. *J. Dairy Sci.*, 73:2702-2710 (1990).

\* cited by examiner

```
Alignment:     1549 C2460 6216-99% con
  0.65 %  1549   Bacillus coagulans
  4.84 %  1548   Bacillus oleronius
  5.36 %  1550   Bacillus smithii
  5.62 %  1548   Bacillus sporothermodurans
  5.65 %  1551   Bacillus badius
  5.79 %  1547   Bacillus firmus
  5.85 %  1547   Bacillus lentus
  5.90 %  1543   Bacillus circulans
  5.95 %  1545   Bacillus niacini
  6.30 %  1548   Bacillus flexus
```

Neighbor Joining Tree

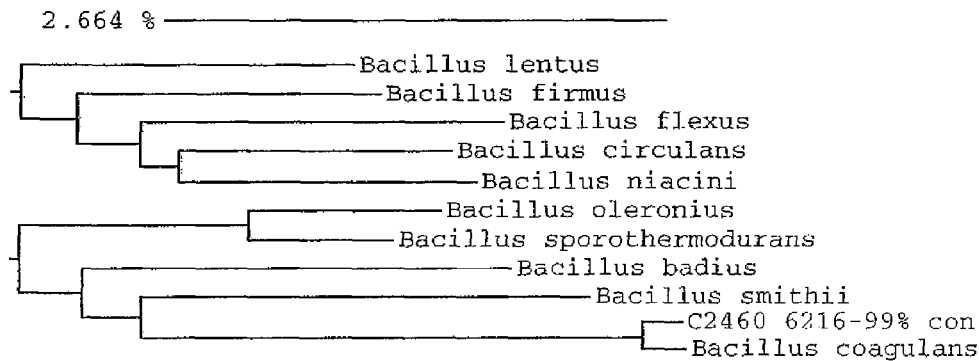

Concise Alignment

```
                        1
               111222222241
               347011256784
               902967240204
C2460 6216-99% con TCGAYTTWTTYC (SEQ ID NO:1; where r = A or G, y = C or T, and w = A or T)
Bacillus coagulans CTRGCGCACCCG (SEQ ID NO:2; where r = A or G, y = C or T, and w = A or T)
```

Fig. 6

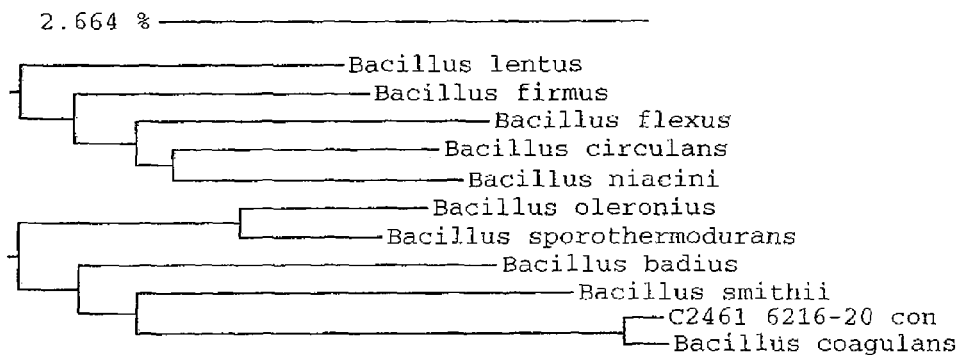

```
Alignment:    1549  C2461 6216-20 con
  0.65 %  1549  Bacillus coagulans
  4.84 %  1548  Bacillus oleronius
  5.36 %  1550  Bacillus smithii
  5.62 %  1548  Bacillus sporothermodurans
  5.65 %  1551  Bacillus badius
  5.79 %  1547  Bacillus firmus
  5.85 %  1547  Bacillus lentus
  5.90 %  1543  Bacillus circulans
  5.95 %  1545  Bacillus niacini
  6.30 %  1548  Bacillus flexus
```

Neighbor Joining Tree

Concise Alignment

```
                    1
          111222222241
          347011256784
          902967240204
C2461 6216-20 con  TCGAYTTWTTYC  (SEQ ID NO:1; where r = A or G, y = C or T, and w = A or T)
Bacillus coagulans CTRGCGCACCCG  (SEQ ID NO:2; where r = A or G, y = C or T, and w = A or T)
```

Fig. 7

```
Alignment:     1549 C2462 6216-30 con
   0.65 %  1549   Bacillus coagulans
   4.84 %  1548   Bacillus oleronius
   5.36 %  1550   Bacillus smithii
   5.62 %  1548   Bacillus sporothermodurans
   5.65 %  1551   Bacillus badius
   5.79 %  1547   Bacillus firmus
   5.85 %  1547   Bacillus lentus
   5.90 %  1543   Bacillus circulans
   5.95 %  1545   Bacillus niacini
   6.30 %  1548   Bacillus flexus
```

Neighbor Joining Tree

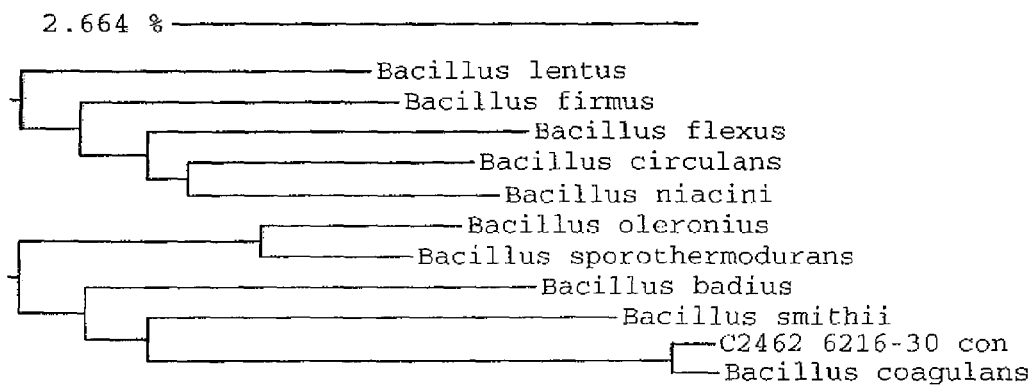

Concise Alignment

```
                                1
                      111222222241
                      347011256784
                      902967240204
C2462 6216-30 con     TCGAYTTWTTYC  (SEQ ID NO:1; where r = A or G, y = C or T, and w = A or T)
Bacillus coagulans    CTRGCGCACCCG  (SEQ ID NO:2; where r = A or G, y = C or T, and w = A or T)
```

Fig. 8

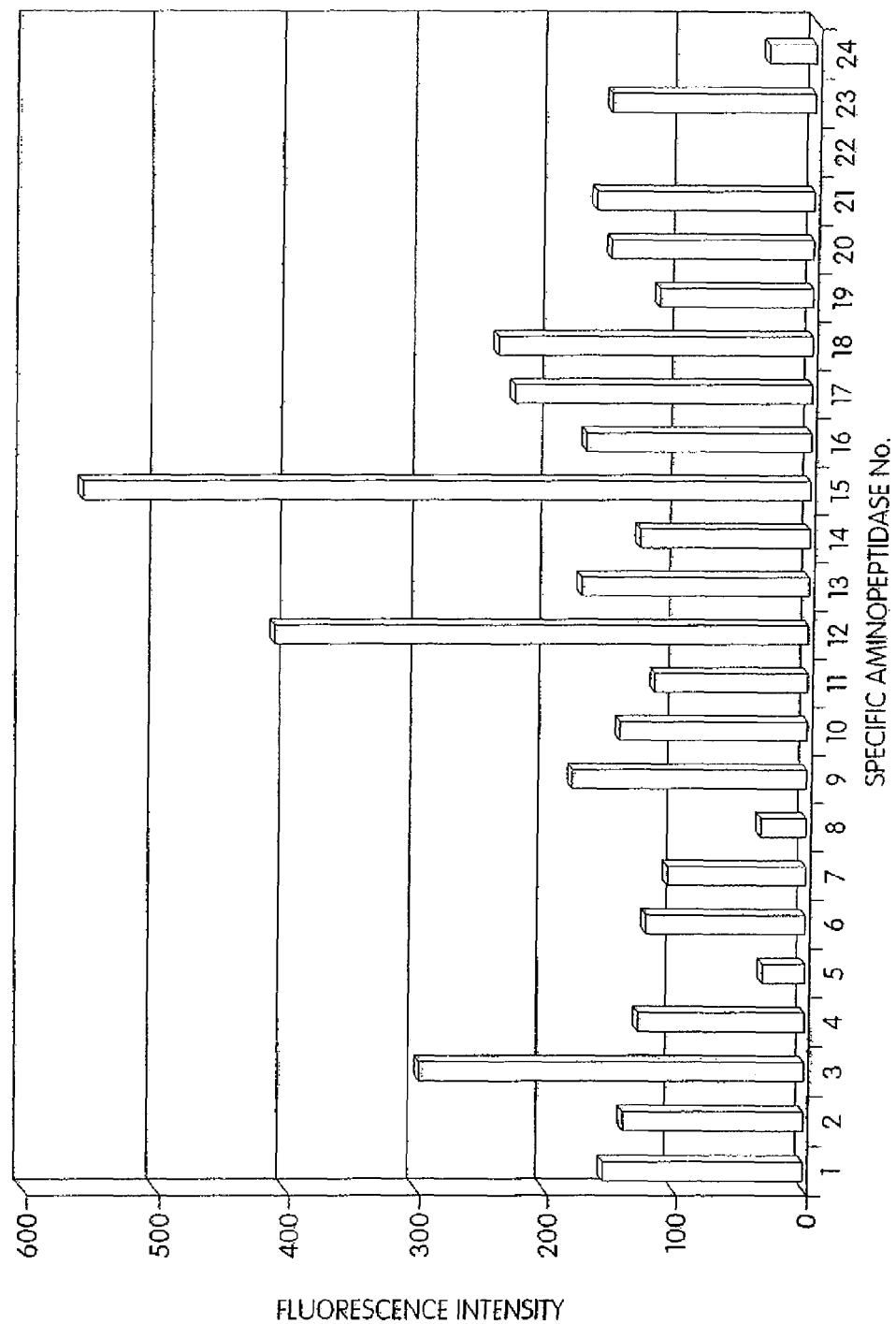

```
SEQUENCE LISTING

<160> NUMBER OF SEQ ID NOS: 2

<210> SEQ ID NO 1
<211> LENGTH: 12
<212> TYPE: DNA
<213> ORGANISM: unidentified bacterium

<400> SEQUENCE: 1
tcgayttwtt yc                                                        12

<210> SEQ ID NO 2
<211> LENGTH: 12
<212> TYPE: DNA
<213> ORGANISM: Bacillus coagulans

<400> SEQUENCE: 2
ctrgcgcacc cg                                                        12
```

INHIBITION OF PATHOGENS BY PROBIOTIC BACTERIA

RELATED APPLICATIONS

This application is a continuation of U.S. Ser. No. 11/706,642, filed Feb. 13, 2007, which is a continuation of U.S. Ser. No. 11/005,897, filed on Dec. 6, 2004, which is a continuation of U.S. Ser. No. 09/708,870, filed on Nov. 8, 2000, which claims priority to U.S. Provisional Application Ser. No. 60/163,959, filed Nov. 8, 1999, entitled: "ISOLATION AND CHARACTERIZATION OF PROBIOTIC STRAINS OF BACILLUS COAGULANS"; and U.S. Provisional Application Ser. No. 60/198,404, filed Apr. 19, 2000, entitled: "ADDITIONAL ISOLATION AND CHARACTERIZATION OF PROBIOTIC STRAINS OF BACILLUS COAGULANS"; the disclosures of which are incorporated herein by reference in their entirety.

FIELD OF THE INVENTION

The present invention relates to methods of treatment and compositions using novel stains of probiotic organisms and/or their extracellular products in therapeutic compositions. More specifically, the present invention relates to the utilization of one or more species or strains of probiotic bacteria and/or their extracellular products for the control of gastrointestinal pathogens, including antibiotic-resistant species.

BACKGROUND OF THE INVENTION

The gastrointestinal microflora has been shown to play a number of vital roles in maintaining gastrointestinal tract function and overall physiological health. For example, the growth and metabolism of the many individual bacterial species inhabiting the gastrointestinal tract depend primarily upon the substrates available to them, most of which are derived from the diet. See, e.g., Gibson et al., 1995. *Gastroenterology* 106: 975-982; Christl, et al., 1992. *Gut* 33: 1234-1238; Gorbach, 1990. *Ann. Med.* 22: 37-41; Reid et al, 1990. *Clin. Microbiol. Rev.* 3: 335-344. These finding have led to attempts to modify the structure and metabolic activities of the community through diet, primarily with probiotics, which are live microbial food supplements. The best-known probiotics are the lactic acid-producing bacteria (i.e., Lactobacilli and *Bifidobacteria*), which are widely utilized in yogurts and other dairy products. These probiotic organisms are non-pathogenic and non-toxigenic, retain viability during storage, and survive passage through the stomach and small intestine. Since probiotics do not permanently colonize the host, they need to be ingested regularly for any health promoting properties to persist. Commercial probiotic preparations are generally comprised of mixtures of Lactobacilli and *Bifidobacteria*, although yeast species such as *Saccharomyces* have also been utilized.

There remains a need for the development of a highly efficacious, non-antibiotic-based therapeutic regimen which functions in acute treatment scenarios, as well as prophylactically to mitigate antibiotic-resistant pathogens (e.g., antibiotic-resistant enterococci) in both humans and animals.

SUMMARY OF THE INVENTION

The invention provides compositions, therapeutic systems, and methods of use which exploit the discovery that novel lactic acid-producing bacterial strains (e.g., the novel strains of *Bacillus coagulans* disclosed herein), or extracellular products thereof, possess the ability to exhibit inhibitory activity in mitigating and preventing the growth and/or colonization rates of pathogenic bacterial, particularly gastrointestinal pathogens such as antibiotic-resistant pathogenic bacterial species including, but not limited to, *Enterococcus, Clostridium, Escherichia, Klebsiella, Campylobacter, Peptococcus, Heliobacter, Hemophylus, Staphylococcus, Yersinia, Vibrio, Shigella, Salmonella, Streptococcus, Proteus, Pseudomonas, Toxoplasmosis*, and *Rotavirus* species, as well as mitigating the deleterious physiological effects of the infection by the pathogen(s). Preferably, the bacteria are probiotic. As currently defined, probiotic microorganisms are those, which confer a benefit when grow in a particular microenvironment by, e.g., directly inhibiting or preventing the growth of other biological organisms within the same microenvironment. Examples of probiotic organisms include, but are not limited to, bacteria, which possess the ability to grow within the gastrointestinal tract, at least temporarily, to displace or destroy pathogenic organisms, as well as providing other benefits to the host. See, e.g., Salminen et al, 1996. *Antonie Van Leeuwenhoek* 70: 347-358; Elmer et al, 1996. *JAMA* 275: 870-876; Rafter, 1995. *Scand. J. Gastroenterol.* 30: 497-502; Perdigon et al, 1995. *J. Dairy Sci.* 78: 1597-1606; Gandi, *Townsend Lett. Doctors & Patients*, pp. 108-110, January 1994; Lidbeck et al, 1992. *Eur. J. Cancer Prev.* 1: 341-353.

In addition, the novel strains of *Bacillus coagulans* disclosed herein possess biochemical and physiological characteristics which include, but are not limited to: (i) the production of the (L)+ optical isomer of lactic acid (propionic acid); (ii) have an optimal growth temperature of between 20-44° C.; (iii) produces spores resistant to temperatures of up to approximately 90° C. which are able to germinate in a human or animal body without specific inducement (e.g., heat-shock or other environmental factors); (iv) the production of one or more extracellular products exhibiting probiotic activity which inhibits the growth of bacteria, yeast, fungi, virus, or any combinations thereof; and/or (v) the ability to utilize a wide spectrum of substrates for proliferation. Preferably, the purified population of *Bacillus coagulans* has an optimal growth temperature of less than 45 degrees C. For example, the isolated population of *Bacillus coagulans* has an optimal growth temperature of 20 degrees C., more preferably 30 degrees C., more preferably 35 degrees C., more preferably 36 degrees C., and most preferably 37 degrees C. In contrast, previously identified populations of *Bacillus coagulans* have an optimal growth temperature of greater than 37 degrees C., e.g., an optimal growth temperature of 45 degrees C. The strain grows at low pH such as pH conditions found in the gastrointestinal tract of a mammal, e.g., pH 2-5.

By purified or isolated preparation of a bacterial strain is meant that the preparation does not contain another bacterial species or strain in a quantity sufficient to interfere with the replication of the preparation at a particular temperature. A purified or isolated preparation of a bacterial strain is made using standard methods, e.g., plating at limiting dilution and temperature selection.

In one embodiment of the present invention, a therapeutic composition comprising *Bacillus coagulans* in a pharmaceutically-acceptable carrier suitable for oral administration to the gastrointestinal tract of a human or animal, is disclosed. In another embodiment, a *Bacillus coagulans* strain is included in the therapeutic composition in the form of spores. In another embodiment, a *Bacillus coagulans* strain is included in the composition in the form of a dried or lyophilized cell mass.

An embodiment of the present invention involves the administration of from approximately $1\times10^3$ to $1\times10^{14}$ CFU of viable, *Bacillus coagulans* vegetative bacteria or spore per day, more preferably from approximately $1\times10^5$ to $1\times10^{11}$, and preferably from approximately $5\times10^8$ to $1\times10^{10}$ CFU of viable, vegetative bacteria or spores per day. Where the condition to be treated involves antibiotic-resistant digestive pathogens and the patient is an adult, the typical dosage is approximately $1\times10^2$ to $1\times10^{14}$ CFU of viable, vegetative bacteria or spores per day, preferably from approximately $1\times10^8$ to $1\times10^{10}$, and more preferably from approximately $2.5\times10^8$ to $1\times10^{10}$ CFU of viable, vegetative bacteria or spores per day.

In another aspect of the present invention, a composition comprising an extracellular product of *Bacillus coagulans* in a pharmaceutically-acceptable carrier suitable for oral administration to a human or animal, is disclosed. In one embodiment, the extracellular product is a supernatant or filtrate of a culture of an isolated *Bacillus coagulans* strain. In another embodiment, the extracellular product is a semi-purified or purified, lyophilized supernatant or filtrate of a culture of an isolated *Bacillus coagulans* strain. In a preferred embodiment, the extracellular product is the active agent(s) possessing the anti-microbial activity, which are isolated and purified from a supernatant or filtrate of a culture of an isolated *Bacillus coagulans* strain.

The extracellular product is administered to a subject in a composition comprising a total concentration ratio of *Bacillus coagulans* extracellular product ranging from approximately 1% to 90% extracellular product with the remainder comprising the carrier or delivery component. The subject is preferably a mammal, e.g., a human. The bacteria and/or products derived from the bacteria are also suitable for veterinary use, e.g., to treat animals such as dogs and cats. A preferred embodiment comprises a composition a total concentration ratio of *Bacillus coagulans* extracellular product ranging from approximately 10% to 75% extracellular product with the remainder comprising the carrier or delivery component.

The present invention is not limited solely to oral administration of the therapeutic compounds disclosed herein. Skin and or mucous membranes are treated using compositions containing *Bacillus coagulans* vegetative cells, spores, or extracellular products produced by vegetative cells. For example, the administration of the *Bacillus coagulans* strains, and/or the extracellular products thereof, aid in the mitigation of vaginal pathogens, as well as reducing the incidence of relapse by re-population of the vagina with these probiotic, lactic acid-producing bacteria. The compositions are used to treat a condition characterized by a reduction or absence of lactic acid-producing bacteria within the vagina, which condition is the a common etiology of both vaginal yeast infections and bacterial vaginosis. Moreover, the use of such probiotic bacterial strains are effective in the mitigation or prevention of pathogens which are resistant to one or more antibiotics. Skin creams, lotions, gels, and the like, which contain *Bacillus coagulans* disclosed herein, and/or the extracellular products thereof, are effective in the mitigation or prevention of pathogenic organisms on the skin, mucus membrane, and cuticular tissues and further reduce the emergence of antibiotic resistant pathogens. In addition to topical and oral administration, the compositions are administered vaginally, intra-ocularly, intra-nasally, intra-otically, or buccally.

A further embodiment of the present invention involves the utilization of probiotic organisms in livestock production, in which antibiotics such as Vancomycin and Gentamicin are commonly used to stimulate health and weight gain. Most, if not all, probiotic organisms are sensitive to these two antibiotics and this fact has limited the potential use of such microorganisms in the livestock industry. In addition, there are many environmentally-related problems associated with the use of antibiotics in livestock production. For example, antibiotic laden animal waste degrades very slowly and the antibiotic residue can persist, further slowing biodegradation. With the addition of species of bacteria that are resistant to Vancomycin, Gentamicin, and other antibiotics, biodegradation is enhanced.

The present invention describes compositions, therapeutic systems, and methods of use for inhibiting pathogen and/or parasite growth in the gastrointestinal tract and feces of animals. According to the invention, there is provided a composition comprising *Bacillus coagulans* vegetative cells or spores in a pharmaceutically- or nutritionally-acceptable carrier suitable for oral administration to the digestive tract of an animal. In another embodiment, the extracellular product from a *Bacillus coagulans* culture is utilized, with or without *Bacillus coagulans* vegetative cells or spores.

In one embodiment, the bacteria is present in the composition at a concentration of approximately $1\times10^3$ to $1\times10^{14}$ colony forming units (CFU)/gram, preferably approximately $1\times10^5$ to $1\times10^{12}$ CFU/gram, whereas in other preferred embodiments the concentrations are approximately $1\times10^9$ to $1\times10^{13}$ CFU/gram, approximately $1\times10^5$ to $1\times10^7$ CFU/g, or approximately $1\times10^8$ to $1\times10^9$ CFU/gram.

In one embodiment, the bacteria is in a pharmaceutically acceptable carrier suitable for oral administration to an animal, preferably, as a powdered food supplement, a variety of pelletized formulations, or a liquid formulation.

The invention also describes a therapeutic system for inhibiting pathogen and/or parasite growth in the gastrointestinal tract and/or feces of an animal comprising a container comprising a label and a composition as described herein, wherein said label comprises instructions for use of the composition for inhibiting pathogen and/or parasite growth.

The advantages of such a non-antibiotic, probiotic bacteria-based therapeutic regimen include, but are not limited to: (i) the administration of the composition will result in the reduction of the colonization rate of enterococci in the gastrointestinal tract; (ii) no contribution to the development of antibiotic resistance; (iii) the composition can be used prophylactically to reduce the reservoir of enterococci in hospitals, which will concomitantly reduce the chances of high-risk patients from acquiring VRE; (iv) the dosage of the composition can be varied according to patient age, condition, etc; and (v) the composition may be utilized in food animal to reduce the development of further antibiotic resistance.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. It should be understood that both the foregoing general description and the following detailed description are exemplary and explanatory only and are not restrictive of the present invention as claimed.

C. isolate (GBI-20); and the 5937-30° C. isolate (GBI-30), in either Trypticase Soy Broth (TSA) or Glucose Yeast Extract (GYE) media.

Figure 2:
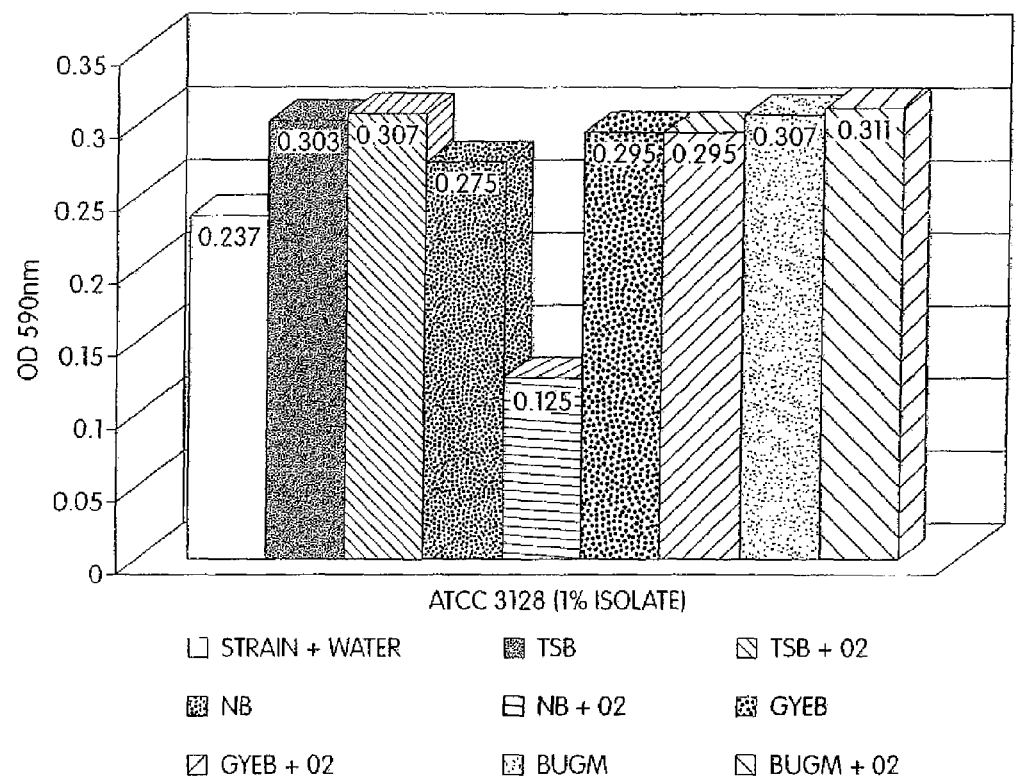

FIG. 2 is a bar graph showing the End-Point Kinetics of the 1% *Bacillus coagulans* strain (GBI-1).

Figure 3:
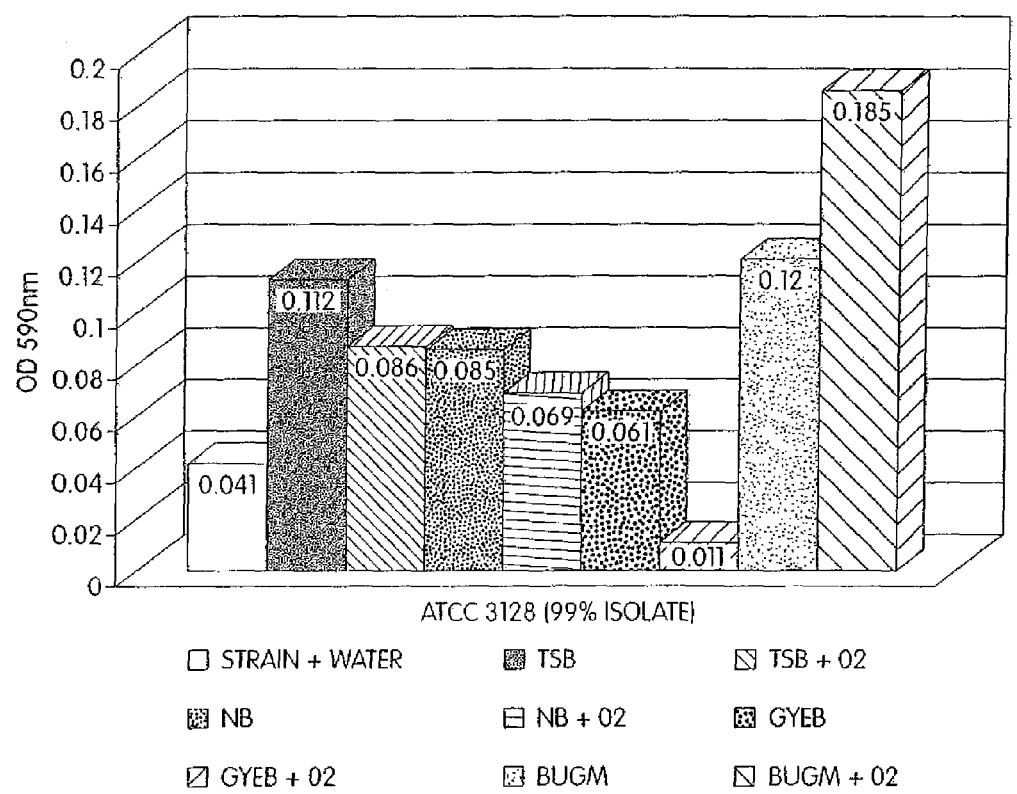

FIG. 3 is a bar graph showing the End-Point Kinetics of the ATCC-=99% *Bacillus coagulans* strain (ATCC #31284).

Figure 4:
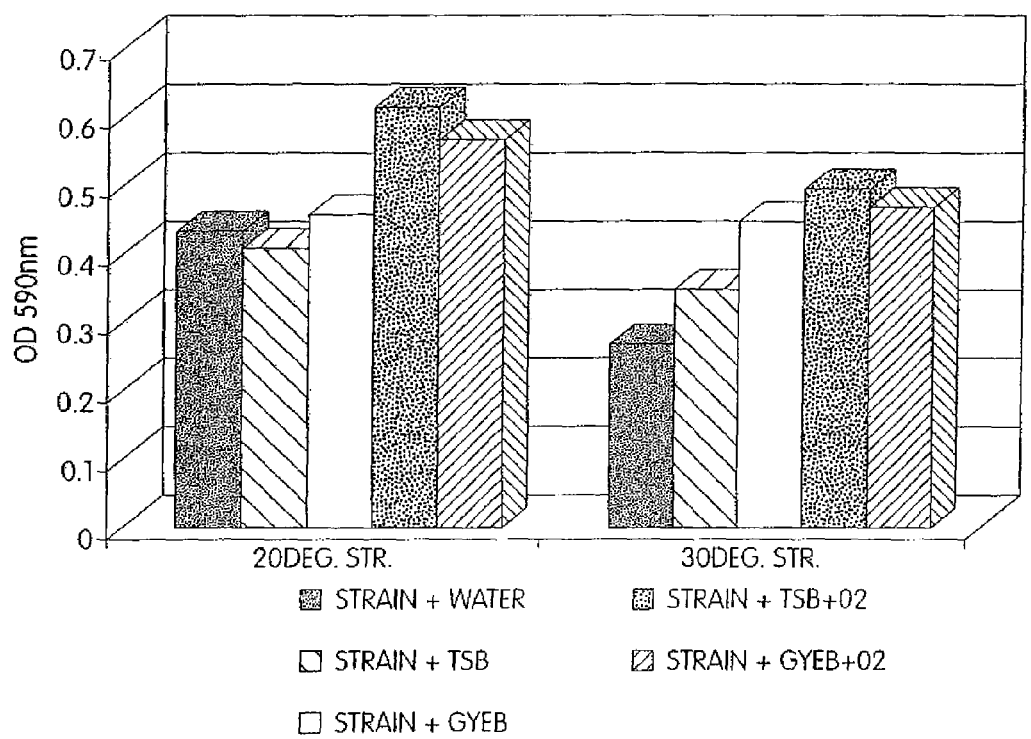

FIG. 4 is a bar graph showing the End-Point Kinetics of the 5937-=20° C. *Bacillus coagulans* strain (GBI-20) and the 5937-=30° C. *Bacillus coagulans* strain (GBI-30) with TSB and GYE media.

Figure 5:
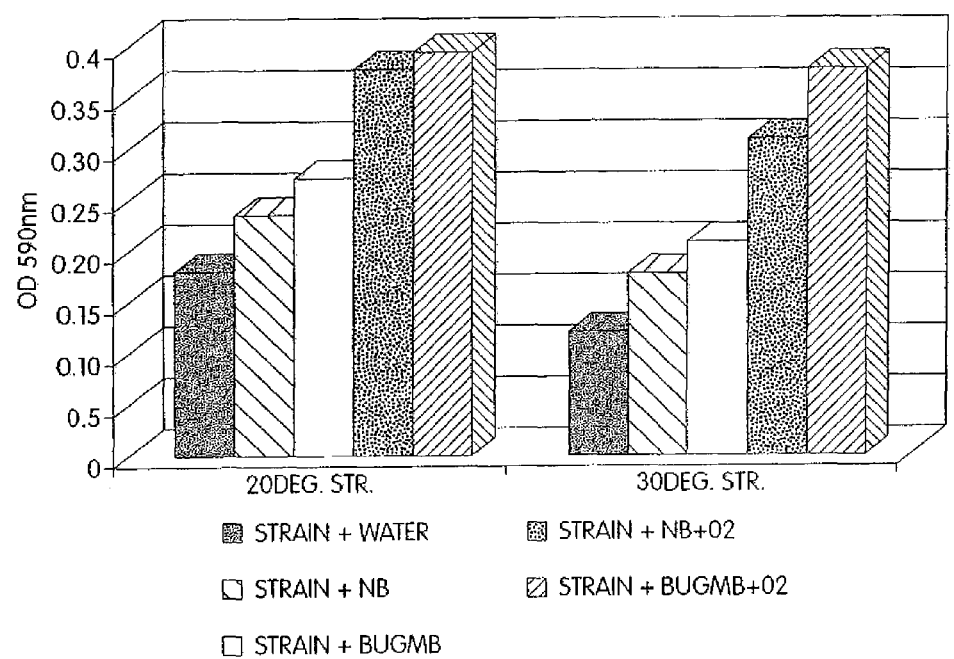

FIG. 5 is a bar graph showing the End-Point Kinetics of the 5937-=20° C. *Bacillus coagulans* strain (GBI-20) and the 5937-=30° C. *Bacillus coagulans* strain (GBI-30) with NB and BUGMB media.

FIG. 6 is a diagram showing the results from Alignment with other *Bacillus* species, Neighbor Joining Tree, and Concise Alignment analysis for the *Bacillus coagulans* ATCC-=99% isolate (ATCC #31284).

FIG. 7 is a diagram showing the results from Alignment with other *Bacillus* species, Neighbor Joining Tree, and Concise Alignment analysis for the *Bacillus coagulans* 20° C. isolate (GBI-20).

FIG. 8 is a diagram showing the results from Alignment with other *Bacillus* species, Neighbor Joining Tree, and Concise Alignment analysis for the *Bacillus coagulans* 30° C. isolate (GBI-30).

Figure 9:
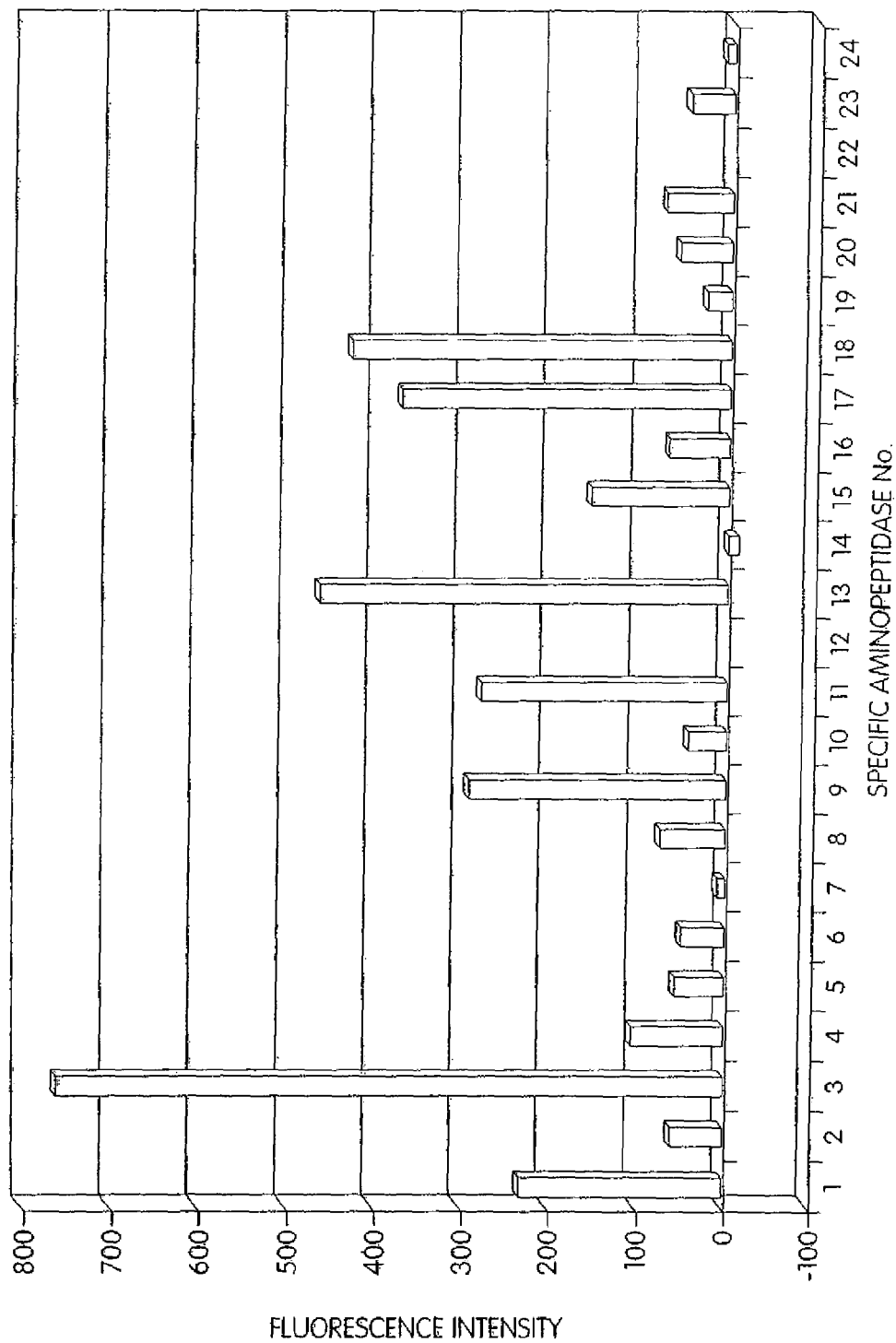

FIG. 9 is a bar graph showing the results of the Aminopeptidase profile for the *Bacillus coagulans* ATCC-=99% isolate (ATCC #31284).

Figure 10:
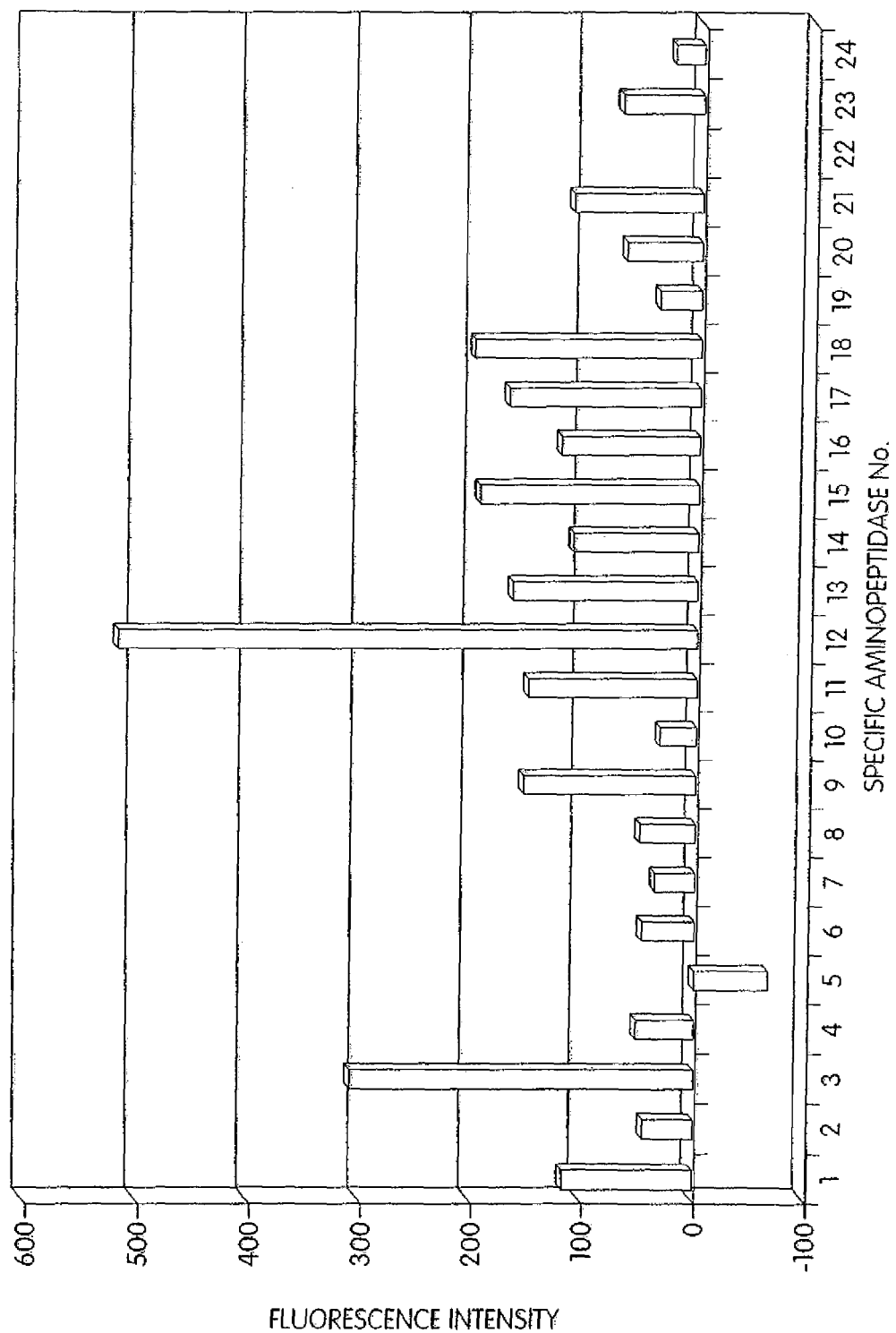

FIG. 10 is a bar graph showing the results of the Aminopeptidase profile for the *Bacillus coagulans* ATCC-=1% isolate (GBI-1).

Figure 11:
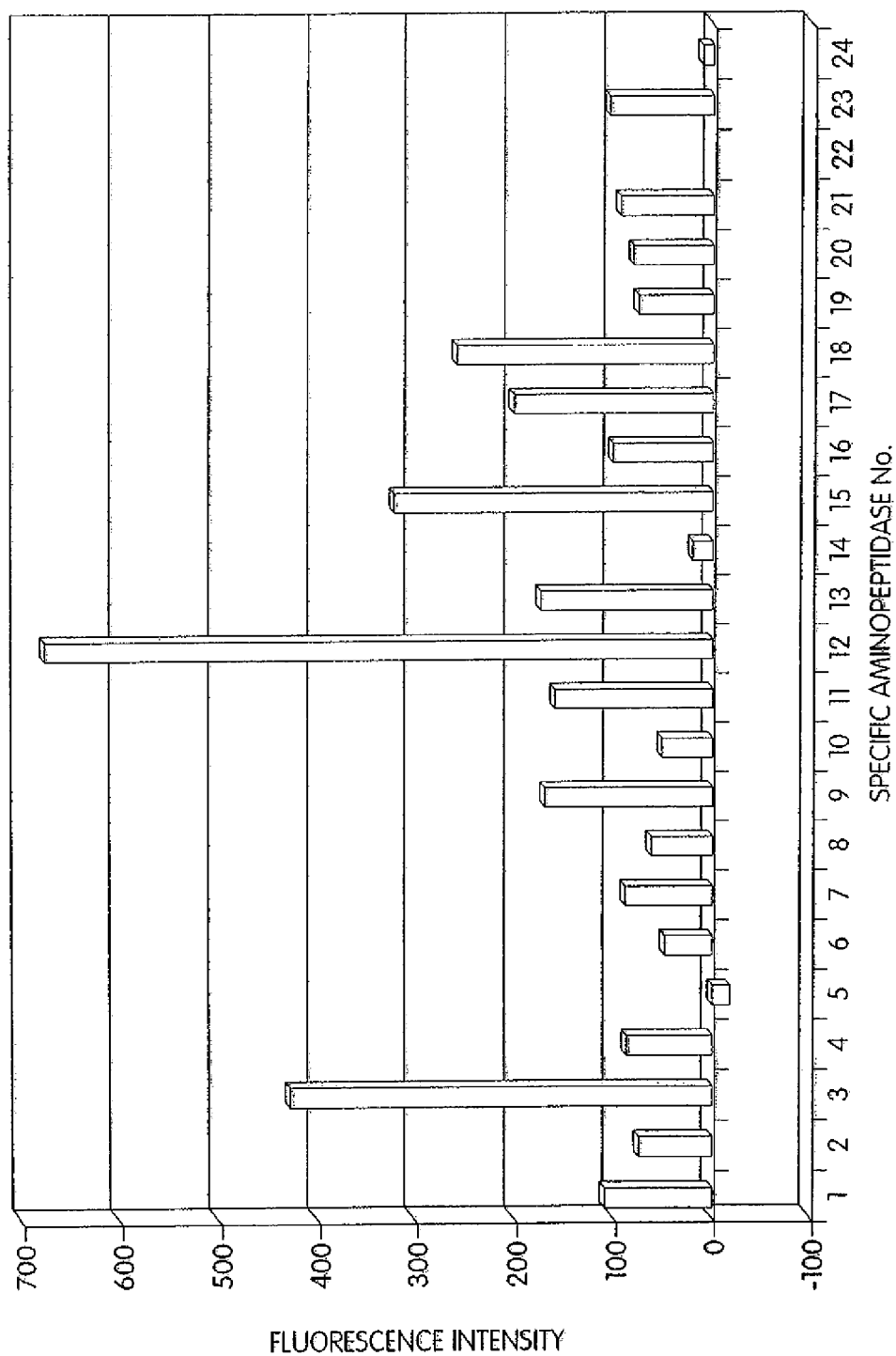

FIG. 11 is a bar graph showing the results of the Aminopeptidase profile for the *Bacillus coagulans* ATCC-=30° C. isolate (GBI-30).

FIG. 12 is a bar graph showing the results of the Aminopeptidase profile for the *Bacillus coagulans* ATCC-=20° C. isolate (GBI-20).

DETAILED DESCRIPTION OF THE INVENTION

Lactic acid-producing bacterial species, e.g., *Lactobacillus*, *Bifidiobacterium*, and the majority of *Bacillus* species have generally been thought to be unsuitable for colonization of the gut due to their instability in the harsh (i.e., acidic) pH environment of the bile, particularly human bile. However, *Bacillus coagulans*, including the novel strains disclosed herein, was found to survive and colonize the gastrointestinal tract such as a bile environment and grown in this low pH range. In particular, the human bile environment is different from the bile environment of animal models, and heretofore there has not been any accurate descriptions of *Bacillus coagulans* growth in human gastrointestinal tract models.

With the current, dramatic increases in the number of bacterial strains, which exhibit resistance to one or more antibiotics, the development of a non-antibiotic-based therapeutic regimen is of paramount importance. Prior to the disclosure of the present invention, there remained a need for the development of a highly efficacious biorational therapy which functions therapeutically in acute treatment scenarios, as well as prophylactically and in vector control applications to mitigate antibiotic-resistant pathogens (e.g., antibiotic-resistant enterococci) in both humans and animals, by the colonization (or re-colonization) of the gastrointestinal tract with probiotic microorganisms, which serves to reduce or prevent both the colonization rate and the potential physiologically deleterious effects due to the colonization of antibiotic-resistant digestive pathogens.

Lactic acid producing bacteria are gram positive and vary in morphology from long, slender rods to short coccobacilli, which frequently form "chains". Their metabolism is fermentative; with some species being aerotolerant (i.e., may utilize oxygen through the enzyme flavoprotein oxidase) while others are strictly anaerobic. Spore-forming lactic acid-producing bacteria are facultative anaerobes, whereas the rest are strictly anaerobic. The growth of these bacteria is optimum at pH 5.5-5.8, and the organisms have complex nutritional requirements for amino acids, peptides, nucleotide bases, vitamins, minerals, fatty acids, and carbohydrates. The lactic acid bacteria have the property of producing lactic acid from fermentable sugars. The genera *Lactobacillus, Leuconostoc, Pediococcus*, and *Streptococcus* are important members of this group. The taxonomy of lactic acid-producing bacteria has been based on the gram reaction and the production of lactic acid from various fermentable carbohydrates. These groups include:

Homofermentative: produce more than 85% lactic acid from glucose.

Heterofermentative: produce only 50% lactic acid and considerable amounts of ethanol, acetic acid and carbon dioxide. Well-known are the hetero-fermentative species, which produce DL-lactic acid, acetic acid and carbon dioxide. These species, which have been used therapeutically, include: *Lactobacillus acidophilus, Lactobacillus plantarum, Lactobacillus casei, Lactobacillus brevis, Lactobacillus delbruekii*, and *Lactobacillus lactis*.

While probiotic preparations were initially systematically evaluated for their effect on health and longevity in the early-1900's (see e.g., Metchinikoff, *Prolongation of Life*, Willaim Heinermann, London 1910), their utilization has been markedly limited since the advent of antibiotics in the 1950's to treat pathological microbes. See, e.g., Winberg, et al, 1993. *Pediatr. Nephrol*. 7: 509-514; Malin et al, *Ann. Nutr. Metab*. 40: 137-145; and U.S. Pat. No. 5,176,911. Unfortunately, the majority of these early studies on probiosis were observational rather than mechanistic in nature, and thus the processes responsible for many probiotic phenomena were not quantitatively elucidated.

There has been an increasing interest in the relationship between intestinal microflora and their effects on the health of the human host. The ecosystem of the human gastrointestinal tract is colonized by more than 500 species of bacteria and represents an extremely complex microenvironment. The composition of the intestinal microflora is constantly changing, being influenced by such factors as: diet, stress, age, and treatment with antibiotics and other drugs.

In order to provide the beneficial effects of lactic acid-producing bacteria, many manufacturers have been marketing various probiotic preparations. The reported health effects of these preparations include effectiveness in the treatment of a variety of disorders including, but not limited to, colitis, constipation, diarrhea, flatulence, gastric acidity, gastroenteritis, gingivitis, hypercholesterolemia, hepatic encephalopathy and tumorigenesis, and in re-colonization of the intestine with beneficial flora after treatment with antibiotics. However, these reports are highly controversial due to such factors as differences in the viability of the implanted flora within the gastrointestinal tract. Successful utilization depends upon the following factors: (i) a high count of viable organisms retaining their viability during manufacturing into dosage forms and subsequent storage; (ii) survival of these lactic acid producing bacteria, once ingested, in the acidic gastric secretions and their passage into the intestine; and (iii) the production of a sufficient quantity of metabolites antagonistic to pathogens (e.g., L(+) (dextrorotatory) lactic acid and bacteriocins).

Previously, numerous species of Lactobacilli have been examined including, but not limited to, *Lactobacillus bulgaricus, Lactobacillus bifidus, Lactobacillus acidophilus, Lactobacillus casei*, and *Lactobacillus brevis*. Interestingly, however, *Lactobacillus acidophilus*, long regarded as the best candidate for therapeutic use, has been subsequently shown to be highly ineffective as a probiotic organism for the re-colonization of the gastrointestinal tract and in the alleviation of gastrointestinal disorders. Moreover, this bacterial strain produces D(−) (levorotatory) lactic acid, which is not an effective antagonistic agent and may potentially introduce metabolic disturbances. In view of this fact, the World Health Organization (WHO) has recommended restricted intake of D(−) lactic acid for adults and total avoidance in infant nutrition.

It is now known that probiotic bacteria mitigate or prevent the growth of putrefactive or pathogenic microorganisms by the process of competitive inhibition, through the generation of a non-physiologically conducive acidic environment (i.e., through the production of lactic or other biological acids) and/or by the production of antibiotic-like substances (i.e., bacteriocins), which are responsible for the bacteria's anti-microbial effects. See, e.g., Klaenhammer, 1993. *FEMS Microbiol. Rev.* 12: 39-85; Barefoot et al., 1993. *J. Diary Sci.* 76: 2366-2379. For example, selected *Lactobacillus* strains, which produce antibiotics, have been demonstrated as effective for the treatment of infections, sinusitis, hemorrhoids, dental inflammations, and various other inflammatory conditions. See, e.g., U.S. Pat. No. 5,439,995. Similarly, *Lactobacillus reuteri* has been shown to produce antibiotics which possess anti-microbial activity against Gram negative and Gram positive bacteria, yeast, and various protozoan. See, e.g., U.S. Pat. Nos. 5,413,960 and 5,439,678. Additionally, the proteolytic, lipolytic, and β-galactosidase activities of probiotic bacteria have also been shown to improve the digestibility and assimilation of ingested nutrients, thereby rendering them valuable in convalescent/geriatric nutrition and as adjuncts to antibiotic therapy.

Probiotics have also been shown to possess anti-mutagenic properties. For example, Gram positive and Gram negative bacteria have been demonstrated to bind mutagenic pyrolysates which are produced during cooking at a high temperature. Studies performed with lactic acid producing bacteria has shown that these bacteria may be either living or dead, due to the fact that the process occurs by adsorption of mutagenic pyrolysates to the carbohydrate polymers present in the bacterial cell wall. See, e.g., Zang, et al., 1990. *J. Dairy Sci.* 73: 2702-2710. Lactobacilli have also been shown to degrade carcinogens (e.g., N-nitrosamines), which may serve an important role if the process is subsequently found to occur at the level of the mucosal surface. See, e.g., Rowland and Grasso, 1986. *Appl. Microbiol.* 29: 7-12. Additionally, the co-administration of lactulose and *Bifidobacteria longum* to rats injected with the carcinogen azoxymethane was demonstrated to reduce intestinal aberrant crypt foci, which are generally considered to be pre-neoplastic markers. See, e.g., Challa, et al., 1997. *Carcinogenesis* 18: 5175-21. Purified cell walls of *Bifidobacteria* may also possess anti-tumorigenic activities in that the cell wall of *Bifidobacteria infantis* induces the activation of phagocytes to destroy growing tumor cells. See, e.g., Sekine, et al., 1994. *Bifidobacteria and Microflora* 13: 65-77. Bifidobacteria probiotics have also been shown to reduce colon carcinogenesis induced by 1,2-dimethylhydrazine in mice when concomitantly administered with fructo-oligosaccharides (FOS; see e.g., Koo and Rao, 1991. *Nutrit. Rev.* 51: 137-146), as well as inhibiting liver and mammary tumors in rats (see e.g., Reddy and Rivenson, 1993. *Cancer Res.* 53: 3914-3918). Interestingly, populations at high risk for colon cancer have been found to harbor gut flora, which efficiently metabolize steroids and hydrolyze glucuronides while concomitantly producing carcinogens (e.g., nitrosamines). A diet containing large concentrations of viable, lactic acid-producing bacteria was found to significantly lower these deleterious bacterial-mediated activities in such individuals.

It has also been demonstrated that the microbiota of the gastrointestinal tract affects both mucosal and systemic immunity within the host. See, e.g., Famularo, et al., Stimulation of Immunity by Probiotics. In: *Probiotics: Therapeutic and Other Beneficial Effects*. pg. 133-161. (Fuller, R., ed. Chapman and Hall, 1997). The intestinal epithelial cells, blood leukocytes, B- and T-lymphocytes, and accessory cells of the immune system have all been implicated in the aforementioned immunity. See, e.g., Schiffrin, et al., 1997. *Am. J. Clin. Nutr.* 66(suppl): 5-20S. Other bacterial metabolic products, which possess immunomodulatory properties, include: endotoxic lipopolysaccharide, peptidoglycans, and lipoteichoic acids. See, e.g., Standiford, 1994. *Infect. Linmun.* 62: 119-125. Accordingly, probiotic organisms are thought to interact with the immune system at many levels including, but not limited to: cytokine production, mononuclear cell proliferation, macrophage phagocytosis and killing, modulation of autoimmunity, immunity to bacterial and protozoan pathogens, and the like. See, e.g., Matsumara, et al., 1992. *Animal Sci. Technol.* (*Jpn*) 63: 1157-1159; Solis-Pereyra and Lemmonier, 1993. *Nutr. Res.* 13: 1127-1140. *Lactobacillus* strains have also been found to markedly effect changes in inflammatory and immunological responses including, but not limited to, a reduction in colonic inflammatory infiltration without eliciting a similar reduction in the numbers of B- and T-lymphocytes. See, e.g., De Simone, et al., 1992. *Immunopharmacol. Immunotoxicol.* 14: 331-340.

While the attachment of probiotics to the gastrointestinal epithelium is an important determinant of their ability to modify host immune reactivity, this is not a universal property of Lactobacilli or *Bifidobacteria*, nor is it essential for successful probiosis. See, e.g., Fuller, 1989. *J. Appl. Bacteriol.* 66: 365-378. For example, adherence of *Lactobacillus acidophilus* and some *Bifidobacteria* to human enterocyte-like CACO-2 cells has been demonstrated to prevent binding of enterotoxigenic and enteropathogenic *Escherichia coli*, as well as *Salmonella typhimurium* and *Yersinia pseudotuberculosis*. See, e.g., Bernet, et al., 1994. *Gut* 35: 483-489; Bernet, et al., 1993. *Appl. Environ. Microbiol.* 59: 4121-4128.

While the gastrointestinal microflora presents a microbial-based barrier to invading organisms, pathogens often become established when the integrity of the microbiota is impaired through stress, illness, antibiotic treatment, changes in diet, or physiological alterations within the G.I. tract. For example, *Bifidobacteria* are known to be involved in resisting the colonization of pathogens in the large intestine. See, e.g., Yamazaki, et al., 1982. *Bifidobacteria and Microflora* 1: 55-60. Similarly, the administration of *Bifidobacteria breve* to children with gastroenteritis eradicated the causative pathogenic bacteria (i.e., *Campylobacter jejuni*) from their stools (see e.g., Tojo, 1987. *Acta Pediatr. Jpn.* 29: 160-167) and supplementation of infant formula milk with *Bifidobacteria bifidum* and *Streptococcus thermophilus* was found to reduce rotavirus shedding and episodes of diarrhea in children who were hospitalized (see e.g., Saavedra, 1994. *The Lancet* 344: 1046-109.

Additionally, lactic acid producing bacteria also are able to colonize the skin and mucus membranes, and may be used either prophylactically or therapeutically to control bacterial infections. For example, lactic acid producing bacteria are able to utilize glycogen in the vaginal epithelial cells to produce lactic acid, which keeps the pH of this environment in the range 4.0 to 4.5. This acidic environment is not conducive for the growth of pathogens such as *Candida albicans, Gardnerella vaginalis*, and various non-specific bacteria, which are responsible for vaginal infections. There is a large body of quantitative evidence, which has demonstrated that the depletion of these lactic acid-producing bacteria is the cause and effect relationship in fungal and bacterial gynecological diseases.

Antibiotic Administration and Production of Multiple Antibiotic-Resistant Pathogenic Bacterial Strains Antibiotics are widely used to control pathogenic microorganisms in both humans and animals. Unfortunately, the widespread use of anti-microbial agents, especially broad-spectrum antibiotics, has resulted in a number of serious clinical consequences. For example, antibiotics often kill beneficial, non-pathogenic microorganisms (i.e., flora) within the gastrointestinal tract, which contribute to digestive function and health. Accordingly, relapse (the return of infections and their associated symptoms) and secondary opportunistic infections often result from the depletion of lactic acid producing and other beneficial flora within the gastrointestinal tract.

Unfortunately, most, if not all, lactic acid-producing or probiotic bacteria are extremely sensitive to common antibiotic compounds. Accordingly, during a normal course of antibiotic therapy, many individuals develop a number of deleterious physiological side-effects including: diarrhea, intestinal cramping, and sometimes constipation. These side-effects are primarily due to the non-selective action of antibiotics, as antibiotics do not possess the ability to discriminate between beneficial, non-pathogenic and pathogenic bacteria, both bacterial types are killed by these agents. Thus, individuals taking antibiotics offer suffer from gastrointestinal problems as a result of the beneficial microorganisms (i.e., intestinal flora), which normally colonize the gastrointestinal tract, being killed or severely attenuated. The resulting change in the composition of the intestinal flora can result in vitamin deficiencies when the vitamin-producing intestinal bacteria are killed, diarrhea and dehydration and, more seriously, illness should a pathogenic organism overgrow and replace the remaining beneficial gastrointestinal bacteria.

Another deleterious result of indiscriminate use of anti-microbial agents is the generation of multiple antibiotic-resistant pathogenic bacterial stains. See, e.g., Mitchell, 1998. *The Lancet* 352: 462-463. For example, a meticillin-resistant *Staphylococcus aurous* (MRSA) strain was responsible for over 50 deaths in a single Australian hospital. See, Shannon, 1998. *Lancet* 352: 490-491. However, these initial reports of MRSA infections have been over-shadowed by the more recent outbreaks of multiple drug resistant (MDR) strains of Enterococci, including vancomycin-resistant Enterococci (VRE). Vancomycin is generally regarded as an antibiotic of "last resort". The development of such resistance has led to numerous reports of systemic infections which remained untreatable with conventional antibiotic therapies.

Multiple Drug-Resistant Enterococci

Vancomycin-resistant enterococci (VRE) have emerged as important nosocomial pathogens in the past decade. First reported in the United States in 1989, these organisms have rapidly spread throughout the country. VRE, particularly *Enterococcus faecium* strains, are often resistant to all antibiotics that are effective for treatment of susceptible enterococci. This situation has left clinicians treating VRE infections with either sub-optimal bacteriostatic agents (e.g., chloramphenicol) or no therapeutic options. Efforts to limit the spread of VRE through infection control measures and reduction of vancomycin use have had a limited effect.

Intestinal colonization with VRE is the most important source for spread of these organisms. Most patients harboring VRE have a-symptomatic intestinal colonization that may persist for months. These patients are at risk to develop VRE infection and are a potential source for spread to healthcare workers, the environment, and to other patients. The infection control measures that are implemented to minimize the spread of VRE are expensive and inconvenient for patients, family members, and healthcare workers.

Recent studies have demonstrated a profound potential for lactic acid producing *Bacillus coagulans* species, especially the novel strains of *Bacillus coagulans* disclosed herein, for use in bio-rational therapies for the prophylactic or therapeutic treatment of antibiotic-resistant digestive pathogens. With the present state of emerging infectious disease and antibiotic-resistance, new therapies and new ways of thinking about controlling pathogens are required. Antibiotics, in some applications, have outlived their usefulness when considering the massive reservoir of new and antibiotic resistant strains that have resulted from the misuse of antibiotics in the healthcare setting and "growth factors" in production animal operations.

Enterococci, leading causes of nosocomial bacteremia, surgical wound infection, and urinary tract infection, are becoming resistant to many and sometimes all standard therapies. New rapid surveillance methods are highlighting the importance of examining enterococcal isolates at the species level. Most enterococcal infections are caused by *Enterococcus faecalis*, which are more likely to express traits related to overt virulence but, at least for the moment, also more likely to retain sensitivity to at least one effective antibiotic. The remaining infections are mostly caused by *Enterococcus faecium*, a species virtually devoid of known overt pathogenic traits but more likely to be resistant to even antibiotics of last resort. Effective control of multiple drug-resistant Enterococci will require: (i) better understanding of the interaction between Enterococci, the environment, and humans; (ii) far more prudent antibiotic use; (iii) better contact isolation in hospitals and other patient care environments; (iv) improved surveillance; and, most importantly, (v) the development of new therapeutic paradigms (e.g., non-antibiotic-based) which are less vulnerable to the cycle of drug introduction and drug resistance.

Two types of Enterococci cause infections: (i) those originating from patients' native flora, which are unlikely to possess resistance beyond that which is intrinsic to the genus and are unlikely to be spread, and (ii) isolates that possess multiple antibiotic resistance traits and are capable of nosocomial transmission. The therapeutic challenge of multiple-drug resistant (MDR) Enterococci (i.e., those strains with significant resistance to two or more antibiotics, often including, but not limited to, vancomycin), has brought their role as important nosocomial pathogens into sharper focus.

During the last decade, enterococci have become recognized as leading causes of nosocomial bacteremia, surgical wound infection, and urinary tract infection. Two types of enterococci are generally found to be associated with causing infections: (i) those originating from patients' native flora, which are unlikely to possess resistance beyond that intrinsic to the genus and are unlikely to be spread from bed to bed; and (ii) isolates that possess multiple antibiotic resistance traits and are capable of nosocomial transmission. The therapeutic challenge of multiple-drug resistant (MDR) enterococci (i.e., those strains with significant resistance to two or more antibiotics, often including, but not limited to, vancomycin) has brought their role as important nosocomial pathogens into sharper focus.

Enterococci normally inhabit the bowel and may be found in the intestine of nearly all animals, from cockroaches to humans. In humans, typical concentrations of enterococci in stool are up to $1 \times 10^8$ CFU per gram. See, e.g., Rice, et al., 1995. Occurrence of high-level aminoglycoside resistance in environmental isolates of enterococci. *Appl. Environ. Microbiol.* 61: 374-376. The predominant species inhabiting the intestine varies. In Europe, the United States, and the Far East, *Enterococcus faecalis* predominates in some instances, and *Enterococcus faecium* in others. Moreover, of the 4 or more known enterococcal species (see, e.g., Devriese, et al., 1993. Phenotypic identification of the genus *Enterococcus* and differentiation of phylogenetically distinct enterococcal species and species groups. *J. Appl. Bacteriol.* 75: 399-408), only *Enterococcus faecalis* and *Enterococcus faecium* commonly colonize and infect humans in detectable numbers with *Enterococcus faecalis* being isolated from approximately 80% of human infections, and *Enterococcus faecium* from the remaining individuals.

Enterococci are exceedingly hardy and tolerate a wide variety of growth conditions, including temperatures of 10° C. to 45° C., and hypotonic, hypertonic, acidic, or alkaline environments. Sodium azide and concentrated bile salts, which inhibit or kill most microorganisms, are tolerated by Enterococci and are actually used as selective agents in agar-based media. As facultative organisms, enterococci grow under reduced or oxygenated conditions, although enterococci are usually considered strict fermenters because they lack a Kreb's Cycle and respiratory chain. However, *Enterococcus faecalis* is an exception since exogenous hemin can be used to produce d, b, and o type cytochromes. *Enterococcus faecalis* cytochromes are only expressed under aerobic conditions in the presence of exogenous hemin and, therefore, may promote the colonization of inappropriate sites.

Enterococci are also intrinsically resistant to many antibiotics. Unlike acquired resistance and virulence traits, which are usually transposon or plasmid encoded, intrinsic resistance is based in chromosomal genes, which typically are non-transferable. Penicillin, ampicillin, piperacillin, imipenem, and vancomycin are among the few antibiotics that show consistent inhibitory, but not bactericidal, activity against *Enterococcus faecalis*. *Enterococcus faecium* is less susceptible to β-lactam antibiotics than *Enterococcus faecalis* because the penicillin-binding proteins of the former have markedly lower affinities for the antibiotics. The first reports of strains highly resistant to penicillin began to initially appear in the 1980s. See, e.g., Bush, et al., 1989. High-level penicillin resistance among isolates of enterococci: implications for treatment of enterococcal infections. *Ann. Intern. Med.* 110: 515-520; Sapico, et al., 1989. Enterococci highly resistant to penicillin and ampicillin an emerging clinical problem. *J. Clin. Microbiol.* 27: 2091-2095.

As will be more-fully discussed below, Enterococci often acquire antibiotic-resistance through exchange of resistance-encoding genes carried on conjugative transposons, pheromone-responsive plasmids, and other broad-host-range plasmids. The past two decades have witnessed the rapid emergence of MDR enterococci. High-level gentamicin resistance was initially reported in 1979 (see, e.g., Horodniceanu, et al., 1979. High-level, plasmid-borne resistance to gentamicin in *Streptococcus faecalis* sub-sp. *zymogens*. *Antimicrob. Agents Chemother.* 16: 686-689), and was quickly followed by numerous reports of nosocomial infection in the 1980's (see, e.g., Zervos, et al., 1987. Nosocomial infection by gentamicin-resistant *Streptococcus faecalis*: an epidemiologic study. *Ann. Intern. Med.* 106: 687-691). Simultaneously, sporadic outbreaks of nosocomial *Enterococcus faecalis* and *Enterococcus facium* infection appeared with penicillin resistance due to β-lactamase production; however, such isolates remain relatively rare. Finally, MDR enterococci that had lost susceptibility to vancomycin were reported in Europe and the United States. See, e.g., Sahm, et al., 1989. In-vitro susceptibility studies of vancomycin-resistant *Enterococcus faecalis*. *Antimicrob. Agents Chemother.* 33: 1588-1591.

Among several phenotypes for vancomycin-resistant enterococci, VanA (resistance to vancomycin and teicoplanin) and VanB (resistance to vancomycin alone) are most common. In the United States, VanA and VanB account for approximately 60% and 40% of vancomycin-resistant Enterococci (VRE) isolates, respectively. See, e.g., Clark, et al., 1993. Characterization of glycopeptide-resistant Enterococci from U.S. hospitals. *Antimicrob. Agents Chemother.* 37: 2311-2317. Inducible genes encoding these phenotypes alter cell wall synthesis and render strains resistant to glycopeptides. It has been demonstrated, in the laboratory, that these genes can be transferred from Enterococci to other bacteria. See, e.g., Arthur, et al., 1993. Genetics and mechanisms for glycopeptide-resistance in Enterococci. *Antimicrob. Agents Chemother.* 37: 1563-1571. For example, *Staphylococcus aureus* has been rendered vancomycin-resistant through apparent transfer of resistance from *Enterococcus faecalis*.

As previously discussed, most enterococci have naturally occurring or inherent resistance to various drugs, including cephalosporins and the semisynthetic penicihinase-resistant penicillins (e.g., oxacillin) and clinically-achievable concentrations of clindamycin and aminoglycosides. Compared with streptococci, most enterococci are relatively resistant to penicillin, ampicillin, and the pseudopenicillins. Many enterococci are also tolerant to the killing effects of cell-wall active agents (e.g., ampicillin, vancomycin, etc.); although recent data suggest that this property may not be inherent, but rather acquired after exposure to antibiotics. For example, the inherent in vivo resistance of *Enterococcus faecalis* to trimethoprim-sulfamethoxazole, may explain the lack of efficacy in animal models. Moreover, bactericidal activity against *Enterococcus faecalis* seems unreliable and very method dependent. In animal models, this combination has not shown good activity and is not generally accepted as an effective anti-enterococcal therapy, especially for systemic infections.

In addition to natural resistance to many agents, enterococci have also developed plasmid- and transposon-mediated resistance to the tetracyclines (e.g., minocycline and doxycycline); erythromycin (e.g., azithromycin and clarithromycin); chloramphenicol; high levels of trimethoprim; and high levels of clindamycin. The propensity of *Enterococcus faecalis* to acquire multiple antibiotic-resistance traits may result from a variety of distinctly different mechanisms for conjugation.

The best-characterized system of conjugation involves pheromone oligopeptides and pheromone-responsive plasmids. See, e.g., Clewell and Keith, 1989. Sex pheromones and plasmid transferin *Enterococcus faecalis*. *Plasmid* 21: 175-184. In this conjugation system, strains of *Enterococcus faecalis* typically secrete into the culture medium a number of different small, oligopeptide sex pheromones which are specific for different types of plasmids. When a cell containing a pheromone-responsive plasmid (i.e., the potential donor cell) comes into contact with its corresponding pheromone, transcription of a gene on the plasmid is turned on, resulting in the synthesis of an aggregation substance on the surface of its cell membrane. When the donor cell, in turn, comes in contact with another *Enterococcus faecalis* bacterium, the aggregation substance (which contains two Arg-Gly-Asp motifs adheres to the binding substance on the surface of most *Enterococcus faecalis* cells, causing them to aggregate. By a process, not yet well-characterized, the pheromone-responsive plasmid can then transfer from the donor bacterium to the other (recipient) bacterium. Once the recipient cell has acquired this particular plasmid, the synthesis of the corresponding sex pheromone is shut-off to prevent self-aggregation. This system of conjugation, which occurs primarily in *Enterococcus faecalis*, is a highly efficient means of plasmid transfer.

Another system of conjugation, also not well-characterized, involves broad host-range plasmids that can transfer among species of enterococci and other gram-positive organisms such as streptococci and staphylococci. See, e.g., Clewell, 1981. Plasmids, drug resistance, and gene transfer in the genus *Streptococcus*. *Microbiol. Rev.* 45: 409-436. The transfer frequency is generally much lower than with the pheromone system. Since staphylococci, streptococci, and enterococci share a number of resistance genes, these broad host-range plasmids may be a mechanism by which some of these resistance genes have spread among different genera.

A third type of conjugation, which involves conjugative transposons, may also explain the spread of resistance genes to many different species. See, e.g., Clewell, 1986. Conjugative transposons and the dissemination of antibiotic resistance in streptococci. *Annu. Rev. Microbial.* 40: 635-659. As opposed to ordinary transposons, which can jump within a cell from one DNA location to another, conjugative transposons also encode the ability to bring about conjugation between different bacterial cells. Since plasmids typically require rather complex machinery for replication (often depending on successful interactions with host proteins) and must face additional problems of surface exclusion and incompatibility, conjugative transposons (which do not replicate, but instead insert into the chromosome or into a plasmid of the new host) appear to be an even more efficient and far-reaching way of disseminating a resistance gene. This may explain why the tetM gene of the conjugative transposon Tn916 has spread beyond the gram-positive species into gram-negative organisms, including gonococci and meningococci, as well as into mycoplasma and ureaplasma. See, e.g., Roberts, 1990. Characterization of the TetM determinants in urogenital and respiratory bacteria. *Antimicrob. Agents Chemother.* 34: 476-478. Other resistance genes, including those encoding resistance to erythromycin and kanamycin, are also found on conjugative transposons; these frequently contain or are related to Tn916. Such transposons may have evolved from a Tn916 ancestor; their emergence suggests the possibility of further dissemination of resistance among gram-positive organisms. Particularly ominous are reports of the vanB gene cluster within large conjugative chromosomal elements that appear similar, at least in function, to conjugative transposons.

Epidemiology of Multiple Drug-Resistant Enterococci

Colonization and infection with MDR enterococci occur worldwide. Early reports showed that in the United States, the percentage of nosocomial infections caused by VRE increased more than 20-fold (i.e., from 0.3% to 7.9%) between 1989 and 1993, indicating rapid dissemination. New database technologies, such as The Surveillance Network (TSN) Database-USA, now permit the assessment of resistance profiles according to species. TSN Database collects and compiles data daily from more than 100 clinical laboratories within the United States, identifies potential laboratory testing errors, and detects emergence of resistance profiles and mechanisms that pose a public health threat (e.g., vancomycin-resistant staphylococci). Data collected by the TSN Database between 1995 and Sep. 1, 1997 were analyzed to determine whether the earlier increase in vancomycin resistance was unique to vancomycin, whether it represented a continuing trend, and whether speciation is quantifiably important in analyzing this trend. Enterococci *faecalis* resistance to ampicillin and vancomycin is uncommon. Little change in resistance prevalence occurred from 1995 to 1997. In contrast, *Enterococcus faecium* vancomycin and ampicillin resistance increased alarmingly. For example, in 1997, 771 (52%) of 1,482 *Enterococcus faecium* isolates exhibited vancomycin resistance, and 1,220 (83%) of 1,474 isolates exhibited ampicillin resistance. Enterococci *faecium* resistance notwithstanding, Enterococci *faecalis* remained by far the most commonly encountered of the two Enterococcal species in TSN Database. Enterococci *faecalis* to Enterococci *faecium* total isolates were approximately 4:1; blood isolates 3:1; and urine isolates 5:1. This observation underscores important differences in the survival strategies and likelihood of therapeutic success, critical factors usually obscured by lumping the organisms together as *Enterococcus* species or enterococci.

Widespread emergence and dissemination of ampicillin and vancomycin resistance in *Enterococcus faecalis* would significantly confound the current therapeutic dilemma. There is little reason to suspect that vancomycin and ampicillin resistances only provide selective advantage for the species *faecium* and not *faecalis*. The relative absence of these resistances in *Enterococcus faecalis* may simply reflect a momentary lack of penetrance and equilibration of the traits. Because of these important differences between the two species, meaningful surveillance of Enterococcal resistance must include species identification.

It has been demonstrated that enterococci account for approximately 110,000 urinary tract infections, 25,000 cases of bacteremia, 40,000 wound infections, and 1,100 cases of endocarditis annually in the United States, with most of these infections occurring in hospitals. Enterococcal infection-related deaths have been difficult to ascertain, due to the fact that severe co-morbid illnesses are common. However, enterococcal sepsis is implicated in up to 50% of fatal cases. Moreover, several recent case-control and historical cohort studies have shown that death risk associated with antibiotic-resistant enterococcal bacteremia is markedly higher than with susceptible enterococcal bacteremia. This trend is predicted to increase, as MDR isolates become more prevalent.

Although exact modes of nosocomial transmission for MDR Enterococci are difficult to ascertain, molecular microbiologic and epidemiological evidence strongly suggest spread between patients, probably on the hands of health-care providers or medical devices, and between hospitals by patients with prolonged intestinal colonization. Numerous outbreaks of MDR Enterococci have been reported; and all but two were due to *Enterococcus faecium*. This disparity, particularly in view of the higher numbers of clinical *Enterococcus faecalis* isolates, may reflect a reporting bias due to the novelty of the combinations of resistance that occur in *Enterococcus faecium*. When isolates from outbreaks of MDR Enterococci have been analyzed by DNA sequencing, more than half have been demonstrated to involve clonally-related isolates.

Prior treatment with antibiotics is common in nearly all patients colonized or infected with MDR Enterococci. See, e.g., Montecalvo, et al., 1994. Outbreak of vancomycin-, ampicillin-, and aminoglycoside-resistant *Enterococcus faecium* bacteremia in an adult oncology unit. *Antimicrob. Agents Chemother.* 38: 1363-1367. Other risk factors include prolonged hospitalization; high severity of illness score; intra-abdominal surgery; renal insufficiency; enteral tube feedings; and exposure to specific hospital units, nurses, or contaminated objects and surfaces within patient-care areas.

Antibiotics may promote colonization and infection with MDR Enterococci by at least two mechanisms. First, many broad spectrum antibiotics have little or no anti-enterococcal activity, and administration commonly leads to overgrowth of susceptible (or resistant) Enterococci at sites at risk for infection. Second, most antibiotics substantially reduce the normal resistance of the intestinal tract to colonization by exogenous organisms. Colonization resistance results primarily from the "limiting action" of the normal anaerobic flora, and to a lesser extent from an intact mucosa, gastric acid secretion, intestinal motility, and intestinal-associated immunity. Antibiotic-induced alterations in the protective flora of the intestine serve as a catalyst for colonization with exogenous pathogens such as MDR Enterococci. Antibiotic restriction programs would be more effective if they included prudent prescribing of all antibiotics, not just single agents (e.g., vancomycin). For example, use of this approach substantially decreased intestinal colonization with VRE in one hospital pharmacy that restricted vancomycin, cefotaxime, and clindamycin use. See, e.g., Quale, et al., 1996. Manipulation of a hospital antimicrobial formulary t control an outbreak of vancomycin-resistant enterococci. *Clin. Infect. Dis.* 23:1020-1025.

Vancomycin Resistance Genetic Elements

In recent years there has been an alarming emergence among Enterococci of acquired resistance to vancomycin. Vancomycin had been in clinical use since the 1950s, although it was not heavily used until the late-1970s and particularly the 1980s. Because multiple bacterial genes are involved in the generation of vancomycin resistance, the development of such resistance was neither easy nor recent.

Vancomycin resistance in enterococci is heterogeneous on many levels. Three phenotypes of vancomycin resistance (designated VanA, VanB, and VanC), each associated with a different ligase, are now well-described; a fourth, type VanD, has been recently reported. See, e.g., Noble, et al., 1992. Co-transfer of vancomycin and other resistance genes from *Enterococcus faecalis* NCTC 12201 to *Staphlococcus aureus. FEMS Microbiol. Lett.* 93: 195-198. VanA- and VanB-type resistance is encoded by gene clusters that are acquired (i.e., not part of the normal genome of enterococci) and are often transferable. VanA-type strains are typically highly resistant to vancomycin and moderately to highly resistant to teicoplanin. This phenotype is often plasmid or transposon mediated and is inducible (i.e., exposure of bacteria to vancomycin results in the induction of the synthesis of several proteins that together confer resistance). See, e.g., Hiramatsu, et al., 1997. Methicillin-resistant *Staphylococcus aureus* clinical strain with reduced vancomycin susceptibility. *J. Antimicrob. Chemother.* 40: 135-146. The VanA gene cluster has been found in a small Tn3-like transposon, Tn1546, and in elements that appear to be closely related (e.g., Tn5488, which has an insertion sequence [IS 1251] within Tn1546. See, e.g., Eliopoulos, et al., 1994. In vitro activities of two glycylcyclines against gram-positive bacteria. *Antimicrob. Agents Chemother.* 38: 534-541. These elements have, in turn, been found on both transferable and nontransferable plasmids, as well as on the chromosome of the host strain.

VanB type resistance was initially not found to be transferable, but at least in some instances, the VanBgene cluster has been found on large (i.e., 90 kb to 250 kb) chromosomally-located transferable elements, one of which contains within it a 64-kb composite transposon (i.e., Tn1547). The VanB-containing 64-kb transposon is part of a 250-kb mobile element shown to move from the chromosome of one *Enterococcus* and insert into the chromosome of another. Although not demonstrated, circularization of the vanB containing large mobile elements resembles the mechanism described for conjugative transposons that can excise from the chromosome of one strain, circularize, transfer from one *Enterococcus* to another, and reinsert into the chromosome of the recipient. The 64-kb transposon can also jump to another plasmid within the host *Enterococcus* and that plasmid can then transfer by conjugation to other bacteria, taking the VanB resistance genes with it.

In contrast, VanC1 and VanC2 are normally occurring genes that are endogenous species characteristics of *F. gaiinarum* and *F. casseliflavus*, respectively, and are not transferable.

Therapeutic Approaches

Suitable antibiotics often are not available to treat MDR enterococcal infections (e.g., endocarditis or bacteremia), in the presence of neutropenia. Combinations of penicillin with vancomycin, ciprofloxacin with ampicillin, or novobiocin with doxycycline, among others, have been used, but can be unpredictable and remain clinically unproven. The substantial drawback of the broad spectrum approach is that the more organisms affected (i.e., both protective commensals as well as pathogens), the more opportunities for resistance to evolve. Broad spectrum antibiotics permit empiric therapy in the absence of a specific diagnosis and generate a more substantial return on investment in the short-term. However, broad-spectrum antibiotics affect not only disease-causing organisms but also commensals present in numbers large enough to generate resistance by otherwise rare mutational or genetic exchange events.

Although there are other therapeutic modalities under development (e.g., targeted therapeutics), so long as the medical and pharmaceutical communities continue to rely upon the use and development of broad-spectrum therapeutics as the principle therapeutic modality, a cycle of drug introduction, followed by emergence of resistance undoubtedly will continue.

With the current, dramatic increases in the number of bacterial strains which exhibit resistance to one or more antibiotics, the development of a non-antibiotic-based therapeutic regimen is of paramount importance. Prior to the disclosure of the present invention, there remained a need for the development of a highly efficacious biorational therapy which functions therapeutically in acute treatment scenarios, as well as prophylactically and in vector control applications to mitigate or slow the development of antibiotic-resistant pathogens (e.g., antibiotic-resistant Enterococci) in both humans and animals, by the colonization (or re-colonization) of the gastrointestinal tract with probiotic microorganisms, which serves to reduce or prevent both the colonization rate and the potential physiologically deleterious effects due to the colonization of antibiotic-resistant digestive pathogens.

In addition to enterococci, the probiotic composition of the present invention is effective against other common or antibiotic-resistant strains of pathogens including, but not limited to, *Candida, Clostridium, Escherichia, Klebsiella, Campylobacter, Peptococcus, Heliobacter, Hemophylus, Staphylococcus, Yersinia, Vibrio, Shigella, Salmonella, Streptococcus, Proteus, Pseudomonas, Toxoplasmosis*, and *Rotovirus* species. The advantages of such a non-antibiotic, probiotic bacteria-based therapeutic regimen include, but are not limited to: (i) the administration of the composition will result reduction of the colonization rate of enterococci in the gastrointestinal tract; (ii) no contribution to the development of antibiotic resistance; (iii) the composition can be used prophylactically to reduce the reservoir of enterococci in hospitals, which will concomitantly reduce the chances of high-risk patients from acquiring VRE; (iv) the dosage of the composition can be varied according to patient age, condition, etc; and (v) the composition may be utilized in a food animal to reduce the development of further antibiotic resistance.

In an additional embodiment, skin creams, lotions, gels, and the like, which contain the novel stains of *Bacillus coagulans* disclosed herein, and/or the extracellular products thereof, would be effective in the mitigation or prevention of pathogenic organisms on the skin, mucus membrane, and cuticular tissues and further reduce the emergence of antibiotic resistant pathogens. By way of example, and not of limitation, the cells, spores, and/or extracellular products from these novel *Bacillus coagulans* strains could be incorporated into these skin products for this express purpose. For example, pathogenic antibiotic-resistant strains of *Pseudomonas, Staphylococcus*, and/or *Enterococcus* are frequently associated with infections of severe burns. Accordingly, the salves, lotions, gels, and the like, combined with the novel *Bacillus coagulans* strains, and/or their extracellular products, as disclosed in the present invention, would be effective in mitigating or preventing these pathogenic organisms. Additionally, administration of these probiotic bacteria would help to achieve a state of proper biodiversity to the skin in burn cases, as, generally, such biodiversity is not associated with pathogenic overgrowth.

Probiotic, Lactic Acid-Producing Bacterial Strains

As utilized herein, "probiotic" refers to microorganisms that form at least a part of the transient or endogenous flora and thereby exhibit a beneficial prophylactic and/or therapeutic effect on the host organism. Probiotics are generally known to be clinically safe (i.e., non-pathogenic) by those individuals skilled in the art. By way of example, and not of limitation to any particular mechanism, the prophylactic and/or therapeutic effect of an acid-producing bacteria of the present invention results, in part, from a competitive inhibition of the growth of pathogens due to: (i) their superior colonization abilities; (ii) parasitism of undesirable microorganisms; (iii) the production of acid (e.g., lactic, acetic, and other acidic compounds) and/or other extracellular products possessing anti-microbial activity; and (iv) various combinations thereof. It should be noted that the aforementioned products and activities of the acid-producing bacteria of the present invention act synergistically to produce the beneficial probiotic effect disclosed herein.

A probiotic bacteria which is suitable for use in the methods and compositions of the present invention: (i) possesses the ability to produce and excrete acidic compounds (e.g., lactic acid, acetic acid, etc.); (ii) demonstrates beneficial function within the gastrointestinal tract; and (iii) is non-pathogenic. By way of example and not of limitation, many suitable bacteria have been identified and are described herein, although it should be noted that the present invention is not to be limited to currently-classified bacterial species insofar as the purposes and objectives as disclosed. The physiochemical results from the in vivo production of lactic acid is key to the effectiveness of the probiotic lactic acid-producing bacteria of the present invention. Lactic acid production markedly decreases the pH (i.e., increases acidity) within the local micro-floral environment and does not contribute to the growth of many undesirable, physiologically-deleterious bacteria and fungi. Thus, by the mechanism of lactic acid production, the probiotic inhibits growth of competing pathogenic bacteria.

Typical lactic acid-producing bacteria useful as a probiotic of this invention are efficient lactic acid producers, which include non-pathogenic members of the *Bacillus* genus which produce bacteriocins or other compounds which inhibit the growth of pathogenic organisms.

The *Bacillus* species, particularly those species having the ability to form spores (e.g., *Bacillus coagulans*), are a preferred embodiment of the present invention. The ability to sporulate makes these bacterial species relatively resistant to heat and other conditions, provides for a long shelf-life in product formulations, and is deal for survival and colonization of tissues under conditions of pH, salinity, and the like within the gastrointestinal tract. Moreover, additional useful properties of many *Bacillus* species include being non-pathogenic, aerobic, facultative and heterotrophic, thus rendering these bacterial species safe and able to readily colonize the gastrointestinal tract.

Preferred methods and compositions disclosed herein utilize novel strains of *Bacillus coagulans* and/or extracellular products thereof as a probiotic. Prior to the invention, it was generally accepted that the various "classic" *Lactobacillus* and/or *Bifidiobacterium* species are unsuitable for colonization of the gut due to their instability in the highly acidic environment of the gastrointestinal tract, particularly the human gastrointestinal tract. The purified *Bacillus coagulans* strains of the present invention are able to survive and colonize the gastrointestinal tract because the optimal temperature for growth is lower than standard known strains of *Bacillus coagulans*. Additionally, probiotic *Bacillus coagulans* is non-pathogenic and is generally regarded as safe (i.e., GRAS classification) by the U.S. Federal Drug Administration (FDA) and the U.S. Department of Agriculture (USDA), and by those individuals skilled within the art.

Because *Bacillus coagulans* possesses the ability to produce heat-resistant spores, it is particularly useful for making pharmaceutical compositions, which require heat and pressure in their manufacture. Accordingly, formulations that include the utilization viable *Bacillus coagulans* spores in a pharmaceutically-acceptable carrier are particularly preferred for making and using compositions disclosed in the present invention.

The growth of these various *Bacillus* species to form cell cultures, cell pastes, and spore preparations is generally well-known within the art. Additionally, the present invention discloses methods for the isolation and partial purification of the extracellular products produced by cultures of *Bacillus coagulans*.

Commercial Sources of Traditional Strains of *Bacillus coagulans*

The Gram positive rods of *Bacillus coagulans* have a cell diameter of greater than 1.0 µm with variable swelling of the sporangium, without parasporal crystal production. *Bacillus coagulans* is a non-pathogenic, Gram positive, spore-forming bacteria that produces L(+) lactic acid (dextrorotatory) under homo-fermentation conditions. It has been isolated from natural sources, such as heat-treated soil samples inoculated into nutrient medium (see e.g., *Bergey's Manual of Systemic Bacteriology*, Vol. 2, Sneath, P. H. A. et al., eds., Williams &

Wilkins, Baltimore, Md., 1986). Purified *Bacillus coagulans* strains have served as a source of enzymes including endonucleases (e.g., U.S. Pat. No. 5,200,336); amylase (U.S. Pat. No. 4,980,180); lactase (U.S. Pat. No. 4,323,651) and cyclomalto-dextrin glucano-transferase (U.S. Pat. No. 5,102,800). *Bacillus coagulans* has also been utilized to produce lactic acid (U.S. Pat. No. 5,079,164). A strain of *Bacillus coagulans* (also referred to as *Lactobacillus sporogenes*; Sakaguti & Nakayama, ATCC No. 31284) has been combined with other lactic acid producing bacteria and *Bacillus natto* to produce a fermented food product from steamed soybeans (U.S. Pat. No. 4,110,477). *Bacillus coagulans* strains have also been used as animal feeds additives for poultry and livestock to reduce disease and improve feed utilization and, therefore, to increase growth rate in the animals (International PCT Pat. Applications No. WO 9314187 and No. WO 9411492). In particular, *Bacillus coagulans* strains have been used as general nutritional supplements and agents to control constipation and diarrhea in humans and animals.

*Bacillus coagulans* cultures have been deposited with the following primary international culture collections: Agricultural Research Service Culture Collection; Russian Collection of Microorganisms; Deutsche Sammlung von Mikroorganismen and Zellkulturen GmbH (German Collection of Microorganisms and Cell Cultures, VKM DSMZ); American Type Culture Collection (ATCC); Finnish Microorganism Collection (University of Goteborg, Sweden); Japan Collection of Microorganisms (JCM); and Japan Federation for Culture Collection.

From the aforementioned deposits there are a total of eight lactic acid-producing bacterial species which have either been: (i) classified and deposited as *Bacillus coagulans* in the past but, have been re-classified as another related *Bacillus* species; or (ii) deposited as another closely related species but, have recently been re-classified as *Bacillus coagulans*. These related species include, but are not limited to, *Bacillus coagulans, Bacillus stereothermophilus, Bacillus thermoacidurans, Lactobacillus sporogenes, Bacillus smithii, Bacillus dextrolacticus, Lactobacillus cereale,* and *Bacillus recemilacticus*. However, there is currently some degree of confusion with respect to the classification of these related bacterial strains—as there are no set rules for optimum, or even appropriate growth parameters, even between similar strains. For example, *Bacillus stereothermophilus* is a *Bacillus* strain known to have an optimum growth of approximately 55° C.

Various *Bacillus coagulans* bacterial strains which are currently commercially available from the American Type Culture Collection (ATCC, Rockville, Md.) include the following accession numbers: *Bacillus coagulans* Hammer NRS 727 (ATCC No. 11014); *Bacillus coagulans* Hammer strain C (ATCC No. 11369); *Bacillus coagulans* Hammer (ATCC No. 31284); and *Bacillus coagulans* Hammer NCA 4259 (ATCC No. 15949). Purified *Bacillus coagulans* bacteria are also available from the Deutsche Sarumlung von Mikroorganismen and Zellkuturen GmbH (Braunschweig, Germany) using the following accession numbers: *Bacillus coagulans* Hammer 1915 (DSM No. 2356); *Bacillus coagulans* Hammer 1915 (DSM No. 2383, corresponds to ATCC No. 11014); *Bacillus coagulans* Hammer (DSM No. 2384, corresponds to ATCC No. 11369); and *Bacillus coagulans* Hammer (DSM No. 2385, corresponds to ATCC No. 15949). *Bacillus coagulans* bacteria can also be obtained from commercial suppliers such as Sabinsa Corporation (Piscataway, N.J.) or K.K. Fermentation (Kyoto, Japan).

These aforementioned *Bacillus coagulans* strains and their growth requirements have been described previously (see e.g., Baker, D. et al, 1960. *Can. J. Microbial.* 6: 557-563; Nakamura, H. et al, 1988. *Int. J. Syst. Bacterial.* 38: 63-73. In addition, various strains of *Bacillus coagulans* can also be isolated from natural sources (e.g., heat-treated soil samples) using well-known procedures (see e.g., *Bergey's Manual of Systemic Bacteriology*, Vol. 2, p. 1117, Sneath, P. H. A. et al., eds., Williams & Wilkins, Baltimore, Md., 1986).

*Bacillus coagulans* had originally been mis-characterized as a *Lactobacillus* in view of the fact that, as originally described, this bacterium was labeled as *Lactobacillus sporogenes* (See, Nakamura et al. 1988. *Int. J. Syst. Bacterial.* 38: 63-73). However, initial classification was incorrect due to the fact that *Bacillus coagulans* produces spores and through metabolism excretes L(+)-lactic acid, both aspects which provide key features to its utility. Instead, these developmental and metabolic aspects required that the bacterium be classified as a lactic acid *Bacillus*, and therefore it was re-designated.

Biochemical Characteristics of *Bacillus coagulans*

*Bacillus coagulans*, being a member of the *Bacillus* genus, is spore-forming which upon activation in the acidic environment of the stomach, can germinate and proliferate in the intestine, produce the favored L(+) optical isomer of lactic acid, and effectively prevent the growth of numerous bacterial and fungal pathogens. Table 1, below, is a comparative chart showing the biochemical attributes of lactic acid-producing bacteria and their similarities.

TABLE 1

| Property | Bacillus Species | Bacillus coagulans | Lactobacillus Species | Spirolactobacillus Species |
|---|---|---|---|---|
| Catalase | + | + | − | − |
| Benzidine | + | N/A | − | − |
| Nitrate Red | + | N/A | − | − |
| Gram Reaction | + | + | + | + |
| Endospores | + | + | − | + |
| Motility | + | + | −[a] | + |
| Lactic Acid | −[b] | + | + | + |
| m-A$_2$PM[c] | + | + | −[a] | + |
| Fatty Acid | Bacillus-Type | Lactobacillus Type | Variable | Undefined |

[a]*Lactobacillus plantarum* may be motile and contains m-A$_2$Mc In Its cell wall
[b]Some species including *Bacillus coagufans* can produce lactic acid
[c]Meso-diaminopimelic acid
[d]Data not Available Known *Lactobacillus* species are generally believed to be unsuitable for colonization of the gut due to their instability in the harsh (i.e., acidic) pH environment of the digestive tract, e.g., in the presence of bile, particularly human bile. This instability is one of the primary reasons why the use of lactic acid-producing bacterial strains as probiotics has not been more vigorously explored.

In contrast to these aforementioned bacterial species, *Bacillus coagulans* is able to survive, colonize, and grow in the gastrointestinal tract. In particular, the human bile environment is different from the bile environment of animal models, and growth of *Bacillus coagulans* in human gastrointestinal tract models has not been described. The following proliferative attributes illustrate the strengths of *Bacillus coagulans* over other species of lactic acid-producing bacteria include, but are not limited to:

Facultative Aerobe: *Bacillus coagulans* possesses the ability to grow well in either environments that have free-oxygen or in strictly anaerobic environments. This is important due to the fact that Lactobacilli and *Bifidobacteria* are not aero-tolerant. Thus, in essence, these aforementioned bacterial species are strictly anaerobic and do not proliferate well in environments containing free-oxygen. Because *Bacillus coagulans* is viable in a free-oxygen environment, it can be used in surface-active formulations (e.g., skin powders, creams, ointments, etc) to act prophylactically against the overgrowth of pathogens.

Thermo-Tolerant: The vegetative cells of *Bacillus coagulans* possess the ability to grow at temperatures as high as 65° C., whereas the endospores can withstand temperatures in excess of 100° C. In fact, *Bacillus coagulans*, along with *Bacillus stereothermophilus*, is used for quality control purposes in autoclaves. This fact is crucial due to the frailty of all Lactobacilli and *Bifidobacteria*. For a bacterium to have commercial viability it must be stabile and viable at the time of packaging. This viability must be retained in order to deliver an efficacious product to the consumer.

Halo-Tolerant: *Bacillus coagulans* possesses the ability to grow in highly alkaline environments including 7% NaCl or 10% caustic soda.

The characteristics of *Bacillus coagulans*, as cited in Bergey's Manual (Seventh Edition), include: Gram-positive spore-forming rods approximately 0.9 μm×3.0-5.0 μm in size; aerobic to microaerophilic; produce L(+) (dextrorotatory) lactic acid in a homofermentative manner. Due to the fact that *Bacillus coagulans* exhibits characteristics typical of both genera *Lactobacillus* and *Bacillus*, its taxonomic position between the families Lactobacillaceae and Bacillaceae has often been discussed.

It is often very difficult to distinguish between two species of bacteria, which are morphologically similar and possess similar physiological and biochemical characteristics. DNA homology analysis is a useful technique in resolving this difficulty. The base composition (i.e., % GC content) and the specific nucleotide sequence of the bacterial DNA generally differs between bacterial species and sub-species. Additionally, DNA from closely related bacteria hybridize with each other more efficiently. It the present invention, these aforementioned methodologies have been effectively employed to differentiate, as well as to recognize the innate resemblance between *Bacillus coagulans* and members of the genus *Lactobacillus* and to validate it's taxonomical placement under genus *Bacillus*.

Table 2, below, discusses the colony morphology of *Bacillus coagulans*.

TABLE 2

Cells are long and slender (0.3 to 0.8 μm), some are bent and all the cells have rounded ends Motile with peritrichous flagellas.
Gram positive.
Colonies are usually 2.5 mm in diameter, convex, smooth, glistening and do not produce any pigment.
Extremely fastidious organisms requiring complex organic substrates for growth such as fermentable carbohydrate, peptone, meat and yeast extract. MRS medium supplemented with tomato juice, manganese, acetate and Tween-80 is a suitable medium for growth.
Grow optimally at 40° C. to 50° C. and the optimum pH in the range 5.5 to 6.2.
Micro-aerophilic, exhibit fermentative metabolism and are facultatively aerobic.
Produce acid from arabinose, xylose, glucose, galactose, mannose, fructose, maltose, sucrose, and trehalose.
Do not hydrolyze starch or casein.
Do not liquefy gelatin.
Are indole negative and do not produce hydrogen sulfide or gas.
Produce L (+) (dextrorotatory) lactic acid from glucose, fructose, sucrose, trehalose.
Menaquinones are absent.

Table 3, below, discusses the mechanism of carbohydrate fermentation utilized by *Bacillus coagulans*:

TABLE 3

| Carbohydrate | Acid Production | Gas Production |
|---|---|---|
| Inulin | − | − |
| Maltose | + | − |
| Mannitol | + | − |
| Raffinose | + | − |
| Sorbitol | − | − |
| Sucrose | + | − |
| Trehalose | + | − |

4. Biological "Safety" of *Bacillus coagulans*

*Bacillus coagulans* enjoys a longer safe history of use than most of the common *Lactobacillus* and *Bifidobacterium* species that are commonly sold as "nutritional supplements" at health food stores, or used in the production of cultured dairy products.

General recognition of biological safety may be based only upon the views of experts qualified by scientific training and experience to evaluate the safety of substances directly or indirectly added to food. The basis of such views may be derived through:

(1) Scientific procedures.
(2) In the case of a substance used in food prior to Jan. 1, 1958, through experience based on common use in food. General recognition of safety requires common knowledge about the substance throughout the scientific community knowledgeable about the safety of substances directly or indirectly added to food.
(3) General recognition of safety based upon scientific procedures shall require the same quantity and quality of scientific evidence as is required to obtain approval of a food additive regulation for the ingredient. General recognition of safety through scientific procedures shall ordinarily be based upon published studies, which may be corroborated by unpublished studies and other data and information.
(4) General recognition of safety through experience based on common use in food prior to Jan. 1, 1958, may be determined without the quantity or quality of scientific procedures required for approval of a food additive regulation. General recognition of safety through experience based on common use in food prior to Jan. 1, 1958, shall be based solely on food use of the substance prior to Jan. 1, 1958, and shall ordinarily be based upon generally available data and information.

Lactic acid-producing bacteria are a necessary component in fermented dairy products. Due to the fact that *Bacillus coagulans* was first isolated in 1932, has been used in the production of food products prior to Jan. 1, 1958, and has not been implicated in any pathogenic or opportunistic diseases since its isolation, it qualifies under as many as 9 sections and subsections of the United States Federal Registry for GRAS (Generally-Regarded as Safe) listing. The GRAS list simply indicates that a food additive is not thought to illicit any toxigenic or pathogenic response and is considered safe by those skilled in the art of food science, biochemistry, and microbiology.

*Bacillus coagulans*, subspecies Hammer (ATCC-31284), was first isolated as a soil isolate at Yamanashi University in 1933 by Nakayama. *Bacillus coagulans* species are usually soil isolate. With the exception of *Bacillus cereus* and *Bacillus anthraices*, *Bacillus* species are known to be benign in the environment. To date, there have been no references of any species of *Bacillus coagulans* being involved in a pathogenic or opportunistic illness. Similarly, in an analysis of published data, there have also been no clinical trials that had been compromised due to pathogenesis by lactic acid-producing bacteria. In view of these facts, which are not disputed within the relevant scientific fields, *Bacillus coagulans* is safe as a therapeutic compositions.

Sensitivity of *Bacillus coagulans* to Antibiotics

Although GRAS-listed organisms are safe for use in "normal", immunocompetent individuals, susceptible individuals (e.g., immunosuppressed, immunocompromised, organ transplant, etc.) may be at risk to develop bacteremia or septicemia through the ingestion of bacterial products that are thought to be biologically safe. Although there have been peer-reviewed articles that have shown Lactobacilli to be implicated in severe systemic infections (i.e., opportunistic pathogenesis), there have been no reports which have shown a *Bacillus coagulans*-mediated etiology. Notwithstanding the foregoing, studies are currently underway in immunocompromised mice/rats to determine whether these novel strains of *Bacillus coagulans* have any potential for such opportunistic pathogenesis.

Analysis of the antibiotic sensitivity of *Bacillus coagulans*, subspecies Hammer (ATCC-31284) was performed using the Kirby-Bauer (counting colonies on plates) and Vitek (optical density of culture) susceptibility testing methodologies in order to ascertain the specific antibiotic compound(s) that would be effective in eliminating a *Bacillus coagulans* colonization, if needed, regardless of rational. Using Kirby-Bauer testing, *Bacillus coagulans* was found to be susceptible to: ampicillin; ciprofloxacin; trimethoprim-sulfamethoxazole; rifampin; erythromycin; vancomycin; gentamicin; oxacillin, and possessed intermediate susceptibility to tetracycline. Using Vitek testing, *Bacillus coagulans* was found to be susceptible to: penicillin; vancomycin; gentamicin (500 µg/ml); streptomycin (2,000 µg/ml); nitrofurantoin; norfloxacin; chloramphenicol, and was resistant to tetracycline. Additionally, Nitrocefin testing was performed and indicated *Bacillus coagulans* was positive for low-level β-lactamase production.

Production of Anti-Microbial Substances by *Bacillus coagulans*

Bacteriocins are proteins or protein-particulate complexes with bactericidal activities directed against species, which are closely related to the producer bacterium. The inhibitory activity of lactic acid-producing bacteria (e.g., *Bacillus coagulans*) towards putrefactive organisms is thought to be partially due to the production of bacteriocins.

Table 4, below, lists some of the various bacterocins, which have been isolated and characterized from lactic acid-producing bacterial species.

TABLE 4

| Bacterocin | Bacterial Species |
| --- | --- |
| Acidolin | *Lactobacillus acidophilus* |
| Adidophilin | *Lactobacillus acidophilus* |
| Lactacin B | *Lactobacillus acidophilus* |
| Lactacin F | *Lactobacillus acidophilus* |
| Bulgarin | *Lactobacillus bulgaricus* |
| Plantaracin SIK-83 | *Lactobacillus plantarum* |
| Plantaracin A | *Lactobacillus plantarum* |
| Lactolin 27 | *Lactobacillus helveticus* |
| Helveticin J | *Lactobacillus helveticus* |
| Reuterin | *Lactobacillus reuteri* |
| Lactobrevin | *Lactobacillus brevis* |
| Lactobacillin | *Lactobacillus brevis* |

Additionally, lactic acid-producing bacteria also inhibit the growth of pathogenic/putrefactive microorganisms through other metabolic products such as hydrogen peroxide, carbon dioxide, and diacetyl.

The metabolites of lactic acid-producing bacteria that exert antagonistic actions against pathogenic bacteria are summarized below in Table 5.

TABLE 5

| Metabolic Product | Mode of Antagonistic Action |
| --- | --- |
| Carbon Dioxide | Inhibits decarboxylation |
| | Reduces membrane permeability |
| Diacetyl | Interacts with arginine-binding proteins |
| Hydrogen peroxide/ Lactoperoxidase | Oxidizes basic proteins |
| Lactic Acid | Undisssociated lactic acid penetrates the membranes, lowering the intracellular pH. Interferes with metabolic processes such as oxidative phosphorylation. |
| Bacterocins | Affects membranes, membrane-associated replication and DNA/protein synthesis. |

The levels of optical isomeric forms of lactic acid produced depend upon the specific species of the bacterium. The structural configurations of these isomers are as follows:

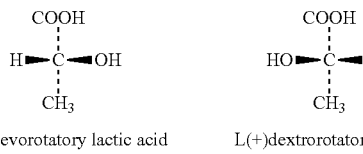

D(-)levorotatory lactic acid     L(+)dextrorotatory lactic acid

In humans, both isomers are absorbed from the intestinal tract. Whereas L(+) lactic acid is completely and rapidly metabolized in glycogen synthesis, D(-) lactic acid is metabolized at a lesser rate and the non-metabolized acid is excreted in the urine. The presence of un-metabolized lactic acid results in metabolic acidosis in infants. *Lactobacillus acidophilus* produces the D(-) form and is therefore of disputable clinical benefit, In contrast, *Bacillus coagulans*, produces only L(+) lactic acid, and hence is preferred over other species of lactic acid-producing bacteria which produce the D(-) form.

Purified Novel Strains of *Bacillus coagulans*

Previously-available strains of lactic acid-producing bacteria (including *Bacillus coagulans* ATCC-type stain #31284) were ineffectual as probiotics due to various factors including, but not limited to, their high optimal growth temperature (i.e., >40° C.) requirement and their requirement for an 80° C. "spore shock" for spore germination. These requirements were incompatible with the use of these previously-available strains of *Bacillus coagulans* as probiotics, in therapeutic compositions (e.g., in the treatment of antibiotic-resistant gastrointestinal pathogens), and the like.

*Bacillus coagulans* described herein possess biochemical and physiological characteristics which include, but are not limited to: (1) the production of the (L)+ optical isomer of lactic acid (propionic acid); (ii) have an optimal growth temperature of less than 45° C.; (iii) the production of spores resistant to temperatures of up to approximately 90° C. which are able to germinate in a human or animal body without specific inducement (e.g., spore-shock or other environmental factors); (iv) the production of one or more extracellular products exhibiting probiotic activity which inhibits the growth of bacteria, yeast, fungi, virus, or any combinations thereof; and/or (v) the ability to utilize a wide spectrum of substrates for proliferation. These novel strains will be more fully discussed, below.

Disclosed herein are three previously uncharacterized strains of *Bacillus coagulans* which have markedly lower growth temperature optima, while still possessing the ability to produce lactic acid and other extracellular products under laboratory fermentation conditions. These novel strains share some characteristics with ATCC-type strain (ATCC-31284), but they possess differences which, e.g., lower growth temperature optima, which increase their efficacy for use as probiotics.

These novel strains were originally discovered in a mixed microbial community of *Bacillus coagulans* colonies where they exhibited differences in both colony morphology and optimal growth temperature from that of the *Bacillus coagulans* ATCC-type strain (hereinafter "ATCC-31284" or "ATCC-99%"). These novel strains are characterized as follows:

*Bacillus coagulans* 1% isolate—designated GBI-1
*Bacillus coagulans* 20° C. isolate—designated GBI-20
*Bacillus coagulans* 30° C. isolate—designated GBI-30
*Bacillus coagulans* 40° C. isolate—designated GBI-40

These novel strains of *Bacillus coagulans* 1% isolate (hereinafter designated "GBI-1"); the *Bacillus coagulans* strain which possesses a optimal growth temperature of 20° C. (hereinafter designated "GBI-20"; the *Bacillus coagulans* strain which possesses a optimal growth temperature of 30° C. (hereinafter designated "GBI-30); and the *Bacillus coagulans* strain which possesses a optima growth temperature of 40° C. (hereinafter designated "GBI-40). The biochemical, physiological, and morphological characteristics of these novel strains of *Bacillus coagulans* will be fully discussed in the Specific Examples section, infra.

Treatment of Antibiotic-Resistant Bacterial Gastrointestinal Infections

The present invention contemplates a method for treating, reducing or controlling antibiotic-resistant bacterial gastrointestinal infections using the therapeutic composition or therapeutic system disclosed herein. The disclosed methods of treatment function so as to inhibit the growth of the pathogenic bacteria which are associated with gastrointestinal infections, as well as to concomitantly mitigate the deleterious physiological effects/symptoms of these pathogenic infections.

The novel strains of *Bacillus coagulans* disclosed herein are generally regarded as safe by those skilled within the art (i.e., GRAS Certified by the FDA) and, therefore, suitable for direct ingestion in food stuffs or as a food supplement. The methods of the present invention comprise administration of a therapeutic composition containing one or more *Bacillus coagulans* strains and/or the extracellular products thereof, to the gastrointestinal tract of a human or animal, to treat or prevent bacterial infection. Administration is preferably made using a liquid, powder, solid food and the like formulation compatible with oral administration, all formulated to contain a therapeutic composition of the present invention by use of methods well-known within the art.

The methods of the present invention includes administration of a composition containing one or more of the following: *Bacillus coagulans* bacterial cells (i.e., vegetative bacterial cells); spores; and/or isolated *Bacillus coagulans* extracellular products (which contains a metabolite possessing antibiotic-like properties) to a human or animal, so as to treat or prevent the colonization of antibiotic-resistant pathogens with the gastrointestinal tract. In particular, for VRE, VISA, PRP, and other pathogens, the methods includes administering to the patient, for example, *Bacillus coagulans* in food or as a food supplement. Oral administration is preferably in an aqueous suspension, emulsion, powder or solid, either already formulated into a food, or as a composition which is added to food by the user prior to consumption. Administration to the gastrointestinal tract may also be in the form of an anal suppository (e.g., in a gel or semi-solid formulation). All such formulations are made using standard methodologies.

Administration of a therapeutic composition is preferably to the gastrointestinal tract using a gel, suspension, aerosol spray, capsule, tablet, powder or semi-solid formulation (e.g., a suppository) containing a therapeutic composition of the present invention, all formulated using methods well-known within the art. Administration of the compositions containing the active probiotic lactic acid-producing bacterium which is effective in preventing or treating a pathogenic bacterial infection, generally consist of one to ten dosages of approximately 10 mg to 10 g of the therapeutic composition per dosage, for a time period ranging from one day to one month. Administrations are (generally) once every twelve hours and up to once every four hours. In the preferred embodiment, two to four administrations of the therapeutic composition per day, of approximately 0.1 g to 5 g per dose, for one to seven days. This preferred dose is sufficient to prevent or treat a pathogenic bacterial infection. Of course, the specific route, dosage and timing of the administration will depend, in part, upon the particular pathogen and/or condition being treated, as well as the extent of said condition.

An embodiment of the present invention involves the administration of from approximately $1\times10^3$ to $1\times10^{14}$ CFU of viable, vegetative bacteria or spore per day, more preferably from approximately $1\times10^5$ to $1\times10^{10}$, and most preferably from approximately $5\times10^8$ to $1\times10^9$ CFU of viable, vegetative bacteria or spores per day. Where the condition to be treated involves antibiotic-resistant digestive pathogens and the patient is an adult, the typical dosage is approximately $1\times10^2$ to $1\times10^{14}$ CFU of viable, vegetative bacteria or spores per day, preferably from approximately $1\times10^8$ to $1\times10^{10}$, and more preferably from approximately $2.5\times10^8$ to $1\times10^{10}$ CFU of viable, vegetative bacteria or spores per day.

Another embodiment of the present invention discloses the administration of a composition comprising a total concentration ratio of *Bacillus coagulans* extracellular product ranging from approximately 1% to 90% extracellular product with the remainder comprising the carrier or delivery component. A preferred embodiment comprises a composition a total concentration ratio of *Bacillus coagulans* extracellular product ranging from approximately 10% to 75% extracellular product with the remainder comprising the carrier or delivery component.

The present invention further contemplates a therapeutic system for treating, reducing and/or controlling pathogenic bacterial infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention.

By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One particularly preferred embodiment comprises unit dose packages of *Bacillus coagulans* spores for use in combination with a conventional liquid product, together with instructions for combining the probiotic with the formula for use in a therapeutic method.

Inhibition of Pathogens and Parasites in Animals

The present invention also discloses compositions and methods of use for inhibiting growth of parasites and/or antibiotic-resistant pathogenic organisms in the gastrointestinal tract of animals. As used herein, the terms "pathogen" and "parasite" are used interchangeably in the context of a deleterious organism growing in the gastrointestinal tract and/or feces of an animal, although it appreciated that these terms have distinctive meanings.

The present invention describes compositions and methods of use for inhibiting or preventing growth of a pathogen in the gastrointestinal tract of an animal comprising the step of administering a composition of the invention to the gastrointestinal tract of the animal one or more of the following: *Bacillus coagulans* bacterial cells (i.e., vegetative bacterial cells); spores; and/or isolated *Bacillus coagulans* extracellular products (which contains a metabolite possessing antibiotic-like properties) to the animal, so as to treat or prevent the colonization of antibiotic-resistant pathogens with the gastrointestinal tract. In particular, for VRE, VISA, PRP, and other pathogens, the methods includes administering to the animal, for example, *Bacillus coagulans* in food or as a food supplement. Oral administration is preferably in an aqueous suspension, emulsion, powder or solid, either already formulated into a food, or as a composition which is added to food by the user prior to consumption. Administration to the gastrointestinal tract may also be in the form of an anal suppository (e.g., in a gel or semi-solid formulation). All such formulations are made using standard methodologies.

The method comprises administration of a composition of this invention containing the active ingredients to an animal in various dosage regimens as described herein to achieve the nutritional result. Administration of the compositions containing the active ingredients effective in inhibiting parasite growth in the intestine and in feces generally consist of one to ten unit dosages of 10 mg to 10 g per dosage of the composition for one day up to one month for an animal of approximately 100 kg body weight. Unit dosages are generally given once every twelve hours and up to once every four hours. Preferably two to four dosages of the composition per day, each comprising about 0.1 g to 50 g per dosage, for one to seven days are sufficient to achieve the desired result.

A preferred method involves the administration into the digestive tract of from $1 \times 10^2$ to $1 \times 10^{10}$ viable bacterium or spore per day, in some embodiments from $1 \times 10^3$ to $1 \times 10^6$, in other embodiments from $1 \times 10^6$ to $1 \times 10^9$, and more preferably about from $5 \times 10^8$ to $1 \times 10^9$ viable bacterium or spore per day. Exemplary dosages range from about $1 \times 10^3$ to $1 \times 10^6$ viable bacterium per day, or alternatively range from about $1 \times 10^6$ to $1 \times 10^9$ viable bacterium per day.

Another embodiment of the present invention discloses the administration of a composition comprising a total concentration ratio of *Bacillus coagulans* extracellular product ranging from approximately 1% to 90% extracellular product with the remainder comprising the carrier or delivery component. A preferred embodiment comprises a composition a total concentration ratio of *Bacillus coagulans* extracellular product ranging from approximately 10% to 75% extracellular product with the remainder comprising the carrier or delivery component.

The method is typically practiced on any animal where inhibiting pathogen or parasites is desired. The animal can be any livestock or zoological specimen where such inhibition of parasites/pathogens provides economic and health benefits. Any animal can benefit by the claimed methods, including birds, reptiles, mammals such as horses, cows, sheep, goats, pigs, and the like domesticated animals, or any of a variety of animals of zoological interest. Other purposes are readily apparent to one skilled in the arts of nutrient absorption, feed utilization and bioavailability.

The present invention further contemplates a therapeutic system for treating, reducing and/or controlling pathogenic bacterial infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention.

By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One particularly preferred embodiment comprises unit dose packages of *Bacillus coagulans* spores for use in combination with a conventional liquid product, together with instructions for combining the probiotic with the formula for use in a therapeutic method.

Insofar as feces provide growth and breeding grounds for undesirable organisms, controlling and/or inhibiting growth of parasites and pathogenic organisms in feces inhibits growth and reproduction of these undesirable organisms in areas where feces is produced, deposited and/or stored. For example, in barns or corrals, in animal cages, in feed lots, in zoological display enclosures, and the like areas where animals are maintained and feces is deposited, there is an opportunity for parasites/pathogens to irritate, spread, reproduce and/or infect other hosts. These circumstances provide a variety of undesirable problems solved by the present invention. For example, it is undesirable for parasites or pathogens to spread and further infect hosts, and thereof or any means to control spread of infection is of great benefit where multiple animals are caged together. In addition, in many circumstances biting of host animals by parasites or flying insects irritates and/or upsets animals, providing behavior problems which includes excessive kicking, biting and related activities which are unsafe for neighboring animals and for animal handlers.

In an another embodiment, the invention contemplates a method for reducing and/or controlling flying insect populations in animal cages/pens/enclosures where animals are maintained comprising administering a composition of the present invention to the gastrointestinal tract of the caged animals.

The present invention is useful at controlling a large variety of parasites and pathogenic organisms, and therefore the invention need not be limited to inhibiting any particular genus or species of organism. For example, based on the mechanisms described herein for effectiveness of the composition, it is seen that all insect varieties which can act as an animal parasite can be targeted by the methods of the present invention. Parasites can infect any of a variety of animals, including mammals, reptiles, birds and the like, and therefore the invention is deemed to not be limited to any particular animal. Examples of well-known or important parasites are described herein for illustration of the invention, but are not to be viewed as limiting the invention. Representative parasites and animal and/or human hosts are described in extensive detail in a variety of veterinary treatises such as "Merck's Veterinary Manual" and "Cecils' Human Diseases" Parasites of horses includes horse bots, lip bots or throat bots, caused by *Gasterophilus* species, such as *G. intestinalis, G. haemorrhiodalis*, and *G. nasalis*, stomach worms, caused by *Habronema* species, such as *H. muscae* or *H. microstoma mulus*, or caused by *Crascia* species, such as *C. mepastoma*, or caused by *Trichostrongvlus* species, such as *T. axei*, ascarids (white worms) caused by *Parascaris* species such as *P. eciuorum*, blood worms (palisade worms, red worms or sclerostomes) caused by *Stroncrvlus* species such as *S. vulcraris, S. epuinus* or *S. edentatus*, small strongyles of the cecum and colon caused by *Triodontophorus* species such as *T. tenuicollis*, pinworms caused by *Oxvuris* species such as *O. eaui*, strongyloides infections of the intestine caused by *Stroncivloides westeri*, tapeworms caused by *Anonlocephala* species such as *A. macma* and *A. perfoliata*, and caused by *Paranonlocephala mamillana*.

Various other parasites cause disease in ruminants, typically cattle, include the wire worm (or barber's pole worm or large stomach worm) caused by *Haemonchus* species. Parasites caused in ruminants, typically swine, include stomach worms caused by *Hvostroncmulus* species.

Additional parasites are known to infect a variety of animal hosts, and therefore are a target for treatment by the methods of the present invention. For example, gastrointestinal parasites infect a variety of animals and can include *Spirocerca* species such as *S. lupi* that cause esopheageal worms in canines and *Physoloptera* species that cause stomach worms in canines and felines.

Where the animal is fed a pelletized or granular food, the composition can be included in the pelletized or granular food, or can comprise a mixture of the pelletized food combined with a pelletized composition of this invention. Mixing pelletized food with a pelletized formulation of a composition of this invention is a particularly preferred method for practicing the present invention, insofar as it provides a convenient system for using commercial feeds and simultaneously regulating the amounts of a composition of this invention to be administered.

Administration of a therapeutic composition is preferably to the gut using a gel, suspension, aerosol spray, capsule, tablet, granule, pellet, wafer, powder or semi-solid formulation (e.g., a suppository) containing a nutritional composition of this invention, all formulated using methods well known in the art.

The present invention further contemplates a system for inhibiting growth of parasites and/or pathogens in the gastrointestinal tract of an animal or in animal feces comprising a container comprising label and a composition according to the present invention, wherein said label comprises instructions for use of the composition for inhibiting pathogen/parasite growth.

Typically, the system is present in the form of a package containing a composition of this invention, or in combination with packaging material. The packaging material includes a label or instructions for use of the components of the package. The instructions indicate the ontemplated use of the package component as described herein for the methods or compositions of the invention.

For example, a system can comprise one or more unit dosages of a therapeutic composition according to the invention. Alternatively, the system can contain bulk quantities of a composition. The label contains instructions for using the composition in either unit dose or in bulk forms as appropriate, and may include information regarding storage of the composition, feeding instruction, health and diet indications, dosages, routes of administration, methods for blending the composition with pre-selected food stuffs, and the like information.

A. Culture of *Bacillus coagulans*

*Bacillus coagulans* is aerobic and facultative, and is typically cultured at pH 5.7 to 6.8, in a nutrient broth containing up to 2% (by wt) NaCl, although neither NaCl, nor KCl are required for growth. A pH of approximately 4.0 to 7.5, is optimum for initiation of sporulation (i.e., the formation of spores). The novel strains of *Bacillus coagulans* disclosed herein are optimally grown at 20° C. to 40° C., and the spores can withstand pasteurization. Additionally, the bacteria exhibit facultative and heterotrophic growth by utilizing a nitrate or sulfate source.

*Bacillus coagulans* can be cultured in a variety of media, although it has been demonstrated that certain growth conditions are more efficacious at producing a culture which yields a high level of sporulation. For example, sporulation is demonstrated to be enhanced if the culture medium includes 10 mg/l of $MgSO_4$ sulfate, yielding a ratio of spores to vegetative cells of approximately 80:20. In addition, certain culture conditions produce a bacterial spore which contains a spectrum of metabolic enzymes particularly suited for the present invention (i.e., production of lactic acid and enzymes for the enhanced probiotic activity and biodegradation). Although the spores produced by these aforementioned culture conditions are preferred, various other compatible culture conditions which produce viable *Bacillus coagulans* spores may be utilized in the practice of the present invention.

Suitable media for the culture of *Bacillus coagulans* include: PDB (potato dextrose broth); TSB (tryptic soy broth); and NB (nutrient broth), which are all well-known within the field and available from a variety of sources. In one embodiment of the present invention, media supplements which contain enzymatic digests of poultry and/or fish tissue, and containing food yeast are particularly preferred. A preferred media supplement produces a media containing at least 60% protein, approximately 20% complex carbohydrates, and approximately 6% lipids. Media can be obtained from a variety of commercial sources, notably DIFCO (Newark, N.J.); BBL (Cockeyesville, Md.); Advanced Microbial Systems (Shakopee, Minn.); and Troy Biologicals (Troy, Md.). An efficacious growth medium for *Bacillus coagulans* is a Glucose Yeast extract (GYE) medium. The formulation for GYE is shown below in Table 6.

TABLE 6

| | |
|---|---|
| Yeast Extract Powder | 5.0 grams |
| Casitone (Peptone) | 5.0 grams |
| D-glucose | 3.0 grams |
| $K_2HPO_4$ | 0.5 grams |
| $KH_2PO_4$ | 0.5 grams |

TABLE 6-continued

| | |
|---|---|
| MgSO$_4$ | 0.3 grams |
| Trace Minerals Solution (see, Table 5) | 1.0 ml |
| Distilled Water | 1000 ml |
| Agar (to be added after pH adjustment) | 15.0 Grams |

The pH of the medium was then adjusted to approximately 6.3 followed by sterilization with steam at 1.2 kg/cm$^2$ pressure at 120° C. for 15 minutes.

The formulation for the trace mineral solution utilized for the analysis of the *Bacillus coagulans* bacterial strain of the present invention is shown below in Table 7.

TABLE 7

| | |
|---|---|
| NaCl | 500 mg |
| MnSO$_4$•5H$_2$O | 500 mg |
| ZnSO$_4$•7H$_2$O | 80 mg |
| CuSO$_4$•5H$_2$O | 80 mg |
| CoSO$_4$•7H$_2$O | 80 mg |
| Distilled Water | 50 ml |

(i) Small-Scale Culture

Small-scale culture of *Bacillus coagulans* may be accomplished by use of the aforementioned Glucose Yeast extract (GYE) medium. The medium was inoculated and grown to a cell density of approximately $1 \times 10^8$ to $1 \times 10^9$ cells/ml. The bacteria were cultured by utilization of a standard airlift fermentation vessel at 30° C. The range of MnSO$_4$ acceptable for sporulation was found to be 1.0 mg/l to 1.0 g/l. The vegetative bacterial cells can actively reproduce up to 65° C., and the spores are stable up to 90° C.

Following culture, the *Bacillus coagulans* bacterial cells or spores were collected using standard methods (e.g., filtration, centrifugation) and the collected cells and spores may subsequently be lyophilized, spray dried, air dried or frozen. As described herein, the supernatant from the cell culture can be collected and used as an extracellular agent secreted by *Bacillus coagulans* which possesses anti-microbial activity useful in a formulation of this invention.

A typical yield obtained from the aforementioned culture methodology is in the range of approximately $1 \times 10^9$-$1 \times 10^{13}$ viable spores and, more typically, approximately $10$-$15 \times 10^{10}$ cells/spores per gram prior to being dried. It should also be noted that the *Bacillus coagulans* spores, following a drying step, maintain at least 90% viability for up to 7 years when stored at room temperature. Hence, the effective shelf-life of a composition containing *Bacillus coagulans* Hammer spores at room temperature is approximately 10 years.

(ii) Large-Scale Culture

Large-scale, batch fermentation of *Bacillus coagulans* may be accomplished by use of the aforementioned Glucose Yeast extract (GYE) medium. The fermentation vessel may include: a 500 liter 314 series stainless airlift fermentation vessel with 60 psi pressure rating; Hanna duel set-point pH control system with in-process electrode; High pressure turbine blower with 0.2 µm in-line filters for sterile air feed; a 10 kw process temperature controller; and appropriate high burst-pressure stainless steel sanitary hose and fittings.

Batch fermentation comprises the following procedure. A single colony of *Bacillus coagulans* was selected with sterile loop from a petri-dish colony. This single colony was then used to inoculate a two-liter Erlenmeyer flask containing GYE media, dextrose, and minerals. The culture was incubated for approximately 18 hours in an orbital shaker (possessing a 2" orbit) at 35° C. This 2 liter culture was used to inoculate a sterilized, 500 liter Batch Fermenter containing GYE media, dextrose, and minerals. The Batch Fermenter was run at 35° C. for approximately 30 hours under high aeration (36-38 LPM). Following this incubation, the Batch Fermenter aeration was turned off and temperature reduced to 20° C. for 4 hours to facilitate settling of the bacterial cells therein. The fermentation broth was harvested using Alpha-Laval Sharples continuous-feed centrifuge at 12,000 rpm at 10° C. and the bacterial solids were removed for subsequent lyophilization.

Preparation of *Bacillus coagulans* Spores

A culture of dried *Bacillus coagulans* spores may be prepared, e.g., as follows. Approximately $1 \times 10^7$ spores were inoculated into one liter of culture medium containing: 30 g (wt./vol GYE media, dextrose, and minerals. The culture was maintained for 72 hours under a high oxygen environment at 37° C. so as to produce a culture having approximately $15 \times 10^{10}$ cells/gram of culture. The culture was then filtered to remove the liquid culture medium and the resulting bacterial pellet was resuspended in water and lyophilized. The lyophilized bacteria were ground to a fine "powder" by use of standard good manufacturing practice (cGMP) methodologies.

Preparation of *Bacillus coagulans* Extracellular Products

A culture of *Bacillus coagulans* was prepared as described in Specific Example A(i)-(ii). The culture was maintained for 5 days as described. The culture was first autoclaved for 30 minutes at 250° F., and then centrifuged at 4000 r.p.m. for 15 mm. The resulting supernatant was collected and subjected to sub-micron filtration by the initial use of a Buchner funnel with a 0.8 µm filter. The filtrate was then collected and further filtered through a 0.2 µm Nalge vacuum filter. The resulting filtrate was then collected (an approximate volume of 900 ml/liter of culture medium) and comprised a liquid containing an extracellular product, which was to be quantitatively analyzed and utilized in the subsequent inhibition studies.

The following methodologies were utilized to characterize the supernatant.

Liquid Chromatography of Proteins: 20 ml of culture supernatant was loaded on an analytical Mono 9 chromatography column (Pharmacia) equilibrated in Buffer A (0.25 M Tris HCl; pH 8.0) using a BioCAD Sprint chromatography system (Perseptive Biosystems, Inc.) running at 2 ml/mm. The column was washed with 15 ml of Buffer A and eluted with a linear gradient ranging from 0% B (i.e., Buffer B is an aqueous 3 M NaCl solution) to 40% B, over a time frame of 12 minutes. The column was then washed with 100% B for 5 minutes. Subsequently, the column was re-equilibrated with Buffer A. Absorbance was monitored at 280 nm to detect elution of aromatic amino acids (i.e., Tyrosine) found in bacterial proteins.

The results demonstrate a mixture of proteins, the majority of which elute at 0.1 M to 0.8 M NaCl, and a minor fraction of material which elutes at a 3.0 M NaCl concentration. Fractions were collected and saved, and dialyzed in Spectrapor dialysis membranes (MW "cut-off" approximately 1,000 Daltons) against water, to facilitate subsequent analysis.

Ultraviolet and Visible Spectroscopy: Differential absorbance spectra were determined between 200 and 600 nm wavelengths in 1 cm quartz cuvettes using a Uvikon 930 scanning spectrophotometer (Kontron Instruments). The baseline was determined with water or culture media.

The results with a water blank showed an absorbance peak at 290 nm to 305 nm for *Bacillus coagulans*, with a significant amount of additional absorbing material found between 210 nm and 400 nm. There was also demonstrated to be significant absorbance in the UV wavelengths, primarily due to presence of protein.

SDS Polyacrylamide Gel Electrophoresis: Electrophoresis was performed by the method of Laemmli (see, Laemmli, 1970. *Nature* 227: 680-685) and the acrylamide gels were poured in 1 mm cassettes (Novex) and run according to recommendations of the commercial supplier (i.e., 120 volts, for 90 minutes [12% gel] and for 2 hours [16%]). The gels were then silver stained by the method of Blum, et al. (see Blum, et al., 1987, *Electrophoresis* 8: 93-99). A 16% acrylamide gel was found to be best resolving the *Bacillus coagulans* proteins. All samples were dialyzed against water prior to preparation for electrophoresis so as to ameliorate salt-associated electrophoretic artifacts. Wide range protein markers (Bio-Rad) were used for protein molecular weight determination.

The electrophoretic results demonstrated a significant number of proteinaceous bands in the ≦4,000 to 30,000 Dalton range for *Bacillus coagulans*.

High Pressure Liquid Chromatography: Five ml of culture supernatants were extracted with 2 ml of acetonitrile, benzene, or 24:1 (v:v) chloroform:isoamyl alcohol for approximately two hours. The phases were allowed to separate for four hours and further separated by centrifugation at 5,000×g for 10 minutes. The organic phase was then filtered through 0.2 μm PVDF filters (Gehnan Acrodisc LC-13) and loaded on an Econosil C-18 10U HPLC column (Altech) in a mobile phase of 20 mM Tris-HCl (pH 7.5). Elution was started after a total of 5 minutes, in a 15 minute linear gradient to 60% acetonitrile (ACN) in water. Elution was continued for 5 minutes in 60% ACN, and the column was then washed and re-equilibrated in 20 mM Tris-HCl (pH 7.5).

The results of reverse-phase HPLC of ACN-extracted *Bacillus coagulans* supernatant demonstrated that increasing the organic character of the solvent led to increasingly "organic profiles" in the HPLC (i.e., an increase in material eluting at higher percentage of ACN) and an increase in the capture of pigmented molecules (i.e., molecules which absorb visible light). These aforementioned molecules will be isolated and further characterized.

The results of these aforementioned analytical methodologies demonstrated that the culture supernatants from *Bacillus coagulans* is very heterogeneous in nature, containing a plurality of proteinaceous and organic molecules. However, the molecules which predominate are the proteins, of which there are a total of 20 distinct species in each of the samples. These protein species can be further fractionated by use of ion exchange chromatography, thus allowing additional characterization. Furthermore, there are also numerous pigmented molecules (i.e., molecules which absorb visible light) that are both highly conjugated (based upon their absorbance at high wavelengths) and hydrophobic (based upon their preference for non-polar solvents and retention on the C-18 HPLC column).

In an embodiment of the present invention, the liquid containing the extracellular product may be formulated into a liquid ointment composition for use in direct application onto dermal, cuticular, or mucous membrane tissues. The liquid ointment was prepared by combining the liquid extracellular product produced above with, e.g., Emu Oil in a ratio of approximately 8:2.

Isolation and Characterization of Novel Strains of *Bacillus coagulans*

Viable Bacterial Colony Isolation and Characterization
Dilution and Heat Treatment Approximately 1 g of a lyophilized *Bacillus coagulans* sample was placed into a surface-sterilized, homogenization container. Approximately 200 ml of sterile physiological saline diluent solution, comprising 8.5 g sodium chloride and 25 mg sodium lauryl sulfate per liter, was then added and the mixture was homogenized at 12,000-15,000 rpm for 5 minutes.

One ml of the homogenized suspension was then transferred into 9.0 ml of sterile physiological saline in a screw-capped tube (25 mm×150 mm size) and mixed thoroughly. This serial dilution was repeated until a final $2 \times 10^{-8}$ dilution was obtained which was designated the "dilution factor." The final diluted tube was then heat-treated in a 70° C. water-bath for 30 minutes, followed by immediate cooling to 45° C.

Plating

Glucose Yeast Extract (GYE) agar medium was liquefied and then cooled to 45° C. in a water-bath. A total of 5 petri dishes per sample were utilized. 1 ml from heat-treated final dilution tube was added into each petri dish, followed by the addition of 5 ml of the above-identified liquefied GYE agar medium into the petri dishes and thorough mixing. When solidified, the plates were incubated in an inverted position at 40° C. for a total of 48 hours.

Counting of Viable Bacterial Colonies

The plates showing 30-300 colonies were selected for counting. Plates possessing a very narrow variation in total colony count were counted and then an average count per plate was calculated. The number of viable cells per gram of sample was obtained by multiplying the average number of colonies counted per plate by the reciprocal of the dilution factor (e.g., if the average number of colonies per plate was 90 and final dilution factor was $2 \times 10^{-6}$, then viable spore count was $90 \times (2 \times 10^6)$ or $1.8 \times 10^{10}$ viable spores per gram.

As will be discussed, infra, subsequent Gas Chromatography Fatty Acid Methyl Ester (GC-Fame) and Biolog™ analyses showed these bacteria to be heretofore uncharacterized strains of *Bacillus coagulans*. Table 8, below, illustrates the differences between the novel strains of *Bacillus coagulans* disclosed herein (i.e., the 20° C. *Bacillus coagulans* isolate (5937-20° C.); 30° C. *Bacillus coagulans* isolate (5937-30° C.); the ATTC 99% *Bacillus coagulans* isolate (ATCC-99%); and the ATTC 1% *Bacillus coagulans* isolate (ATCC-1%), wherein (−) indicates no growth; (+) indicates light or minimal growth; and (++) indicates excellent or optimal growth. Glucose Yeast Extract (GYE) media and Trypticase Soy Broth (TSB) culture media were used.

TABLE 8

| Strain | Media Type | Incubation Temperature |
|---|---|---|
|  |  | 30° C. |
|  |  | 35° C. |
|  |  | 40° C. |
| ATCC-99% Isolate | GYE | − |
|  | TSA | − |
|  |  | + |
|  |  | + |
| 1% Isolate (GBI-1) | GYE | − |
|  | TSA | − |
|  |  | + |
| 5937-20° C. Isolate (GBI-20) | GYE | + |
|  | TSA | ++ |
| 5937-30° C. Isolate (GBI-30) | TSA | ++ |
|  |  | − |
|  |  | + |
|  |  | ++ |
|  |  | ++ |
|  |  | ++ |

Figure 1:
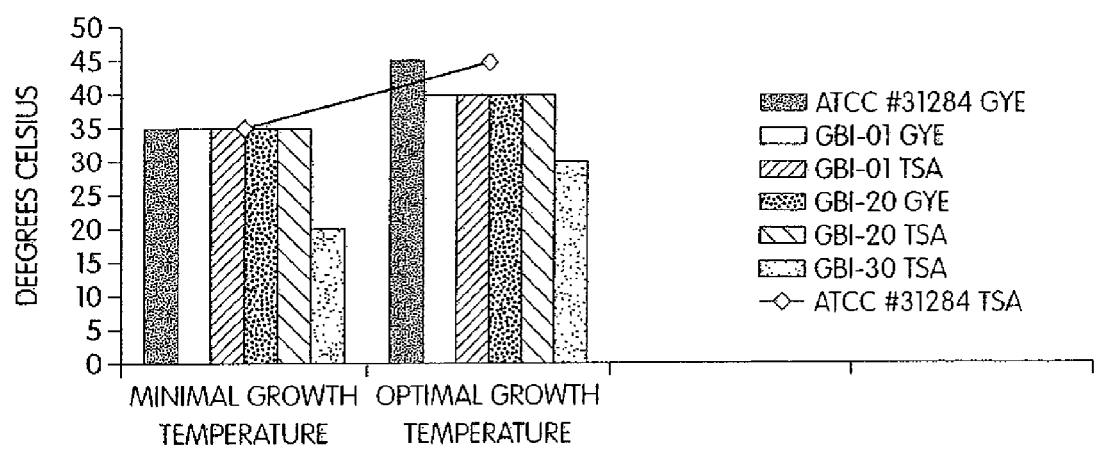
FIG. 1 is a bar graph showing the minimal and optimal culture temperatures for the *Bacillus coagulans* 1% isolate (GBI-1); ATCC-=99% isolate (ATCC #31284); the 5937-20°

FIG. 1 illustrates, in histogram form, the minimal and optimal culture temperatures for the *Bacillus coagulans* 1% isolate (GBI-1); ATCC-99% isolate; the 5937-20° C. isolate (GBI-20); and the 5937-30° C. isolate (GBI-30), in either Trypticase Soy Broth (TSA) or Glucose Yeast Extract (GYE) media.

pH Kinetic Studies

Materials and Methods:

A total of four cultures of *Bacillus coagulans* strains were analyzed with pH Kinetic Testing, Heterotrophic Plate Counts, and Optical Density (OD) in % Optical Transmittance of culture growth at 4 hour intervals for 28 hours in tryptic soy broth (TSB) media. These stains included: the 20° C. *Bacillus coagulans* isolate (GBI-20); 30° C. *Bacillus coagulans* isolate (GBI-30); the ATTC 99% *Bacillus coagulans* isolate (ATCC-99%); and the 1% *Bacillus coagulans* isolate (GBI-1).

Each of the aforementioned bacterial stains were placed in 50 ml Erlenmeyer flasks containing 20 ml of TSB media. Seven flasks were prepared for each of the four isolates, one for each 4 hour interval of the 28 hour study. Initial seed cultures were broth cultures in test tubes, which had a % transmittance of 10%. 1.0 ml of this culture was then place into each of the 28 total flasks, representing 7 flasks for each strain. These inoculated flasks were incubated on a rotary environmental shaker at 45° C. for 28 hours. Every 4 hours, the shaker was stopped, and the new culture removed for evaluations. OD readings in % Optical Transmittance, pH, and Total Heterotrophic Plate Counts by 3M Petrifilm spread plate method performed to monitor bacterial cell density and pH changes at these different time intervals. The results of the pH evaluations, OD in % Transmittance, and Total Heterotrophic Plate Counts are shown below in Table 9, Table 10, and Table 11, respectively.

TABLE 9

Data: pH readings of broth culture

| PH | GBI-20 | GBI-30 | ATTC-99% | GBI-1 |
| --- | --- | --- | --- | --- |
| 4 Hour | 7.0 | 7.0 | 7.0 | 7.1 |
| 8 Hour | 6.4 | 6.4 | 6.6 | 6.5 |
| 12 Hour | 6.6 | 6.4 | 6.4 | 6.5 |
| 16 Hour | 6.4 | 6.5 | 6.4 | 6.5 |
| 20 Hour | 6.8 | 7.0 | 6.9 | 6.9 |
| 24 Hour | 7.6 | 7.4 | 7.4 | 7.3 |
| 28 Hour | 7.6 | 7.9 | 7.8 | 7.8 |

TABLE 10

Data: % light transmittance readings through broth culture

| | GBI-20 | GBI-30 | ATTC 99% | GBI-1 |
| --- | --- | --- | --- | --- |
| 4 Hour | 68 | 51 | 62 | 65 |
| 8 Hour | 8 | 6.5 | 8 | 8 |
| 12 Hour | 4 | 3.0 | 3.5 | 4 |
| 16 Hour | 40* | 38* | 36* | 44* |
| 20 Hour | 37* | 33* | 33* | 37* |
| 24 Hour | 50* | 31* | 34.5* | 34* |
| 28 Hour | 33* | 32* | 30* | 34* |

*1:10 dilution of broth culture in sterile distilled water

TABLE 11

Total Heterotrophic Plate Counts by Spread Plate Method of $10^6$ Dilution

| | GBI-20 | GBI-30 | ATTC 99% | GBI-1 |
| --- | --- | --- | --- | --- |
| 4 Hour | $2.2 \times 10^7$ | $3.9 \times 10^7$ | $2.5 \times 10^7$ | $1.7 \times 10^7$ |
| 8 Hour | $4.9 \times 10^7$ | $3.6 \times 10^8$ | $1.8 \times 10^8$ | $3.6 \times 10^8$ |
| 12 Hour | $7.2 \times 10^8$ | $2.0 \times 10^8$ | $9.0 \times 10^8$ | $9.0 \times 10^8$ |
| 16 Hour | TNTC | TNTC | TNTC | $5.2 \times 10^8$ |
| 20 Hour | $5.0 \times 10^8$ | $2.4 \times 10^8$ | $9.9 \times 10^7$ | $3.4 \times 10^8$ |
| 24 Hour | $3.0 \times 10^8$ | $3.0 \times 10^8$ | $1.1 \times 10^8$ | $3.8 \times 10^8$ |
| 28 Hour | $7.0 \times 10^8$ | $9.2 \times 10^7$ | $2.8 \times 10^8$ | $6.8 \times 10^8$ |

Experimental Results

As may be ascertained from Tables 9-11, there are distinct variances between all isolates in regard to L(+) lactic acid production at different intervals. The interval corresponding cell density was determined using light transmittance using a Vitek machine operating at either 540 or 680 nm and a standard plate count on TSB. The 20° C. *Bacillus coagulans* isolate (GBI-20) and the 30° C. *Bacillus coagulans* isolate (GBI-30) provided higher growth rates and were markedly more efficient at lowering the pH of the fermentation broth at the 8 hour interval and afterwards (using TSB as a fermentation substrate), than the 1% *Bacillus coagulans* isolate (GBI-1) and the ATTC 99% *Bacillus coagulans* isolate. These results would seem to indicate that these aforementioned strains are effective in mitigating diseases that are pH-specific such as *Escherichia, Campylobacter, Candida, Clostridium*, and *Staphylococcus*, than either the 1% *Bacillus coagulans* isolate (GBI-1) and the ATTC 99% *Bacillus coagulans* isolate.

Growth/End-Point Kinetic Studies

GBI-1 and ATCC-99% *Bacillus coagulans* Isolates

Two cultures of *Bacillus coagulans* strains were analyzed with Growth/End-Point Kinetic Testing. These stains included: the 1% *Bacillus coagulans* isolate (GBI-1) and the ATCC-99% *Bacillus coagulans* isolate.

In Kinetic Assays No. 1, the 1% *Bacillus coagulans* strain (GBI-1) was tested. In Kinetic Assay No. 2, the ATCC-99% *Bacillus coagulans* strain was tested. The specific strain of *Bacillus coagulans* to be tested was grown for a total of 48 hours in Trypticase Soy Broth (TSB) medium at 45° C. Following incubation, the cultures were suspended in sterile saline to a turbidity (T) of approximately 40-50% T. The diluted cultures were placed into the wells of a 96-well microtiter plate which contained a specific growth medium which comprised one of the following: TSB, Glucose Yeast Extract (GYE) medium, or, either with or without additional oxygenation. To oxygenate the growth medium, 100 ml of each medium was placed under the flow of an oxygen concentrator at a rate of 4 liters/minute for a total of 15 minutes. In addition, each microplate well also contained a tetrazolium dye/redox indicator system. Bacterial growth (i.e., metabolic respiration or oxidation of carbon sources) was monitored by tetrazolium reduction as measured at 590 nm in a spectrophotometric microplate reader.

Bacterial growth was measured every 20 minutes during a total incubation of 22 hours at 32° C. The kinetic data was processed and the background blank values subtracted.

Following completion of the above-referenced Kinetic Growth Assay, the tetrazolium reduction as measured at 590 nm in the microplate is read as an End-Point Kinetic assay. FIG. 2 and FIG. 3 show the End-Point Kinetics of both the 1% *Bacillus coagulans* strain (GBI-1) and the ATCC-99% *Bacillus coagulans* strain, respectively.

5937-20° C. and 5937-30° C. *Bacillus coagulans* Isolates

Two cultures of *Bacillus coagulans* strains were analyzed with Growth/End-Point Kinetic Testing. These stains included: the 20° C. *Bacillus coagulans* isolate (GBI-20) and the 30° C. *Bacillus coagulans* isolate (GBI-30).

In Kinetic Assays No. 3, the 20° C. *Bacillus coagulans* isolate (GBI-20) was tested. In Kinetic Assay No. 4, the 30° C. *Bacillus coagulans* isolate (GBI-30) was tested. The specific strain of *Bacillus coagulans* to be tested was grown for a total of 48 hours in Glucose Yeast Extract (GYE) medium at 35° C. Following incubation, the cultures were suspended in sterile saline to a turbidity (T) of approximately 40-50% T. The diluted cultures were placed into the wells of a 96-well microtiter plate which contained a specific growth medium which comprised one of the following: GYE or Trypticase Soy Broth, Nutrient Broth (NB), or Biolog Universal Growth Medium (BUGMB), either with or without additional oxygenation. To oxygenate the growth medium, 100 ml of each medium was placed under the flow of an oxygen concentrator at a rate of 4 l/minute for a total of 15 minutes. In addition, each microplate well also contained a tetrazolium dye/redox indicator system. Bacterial growth (i.e., metabolic respiration or oxidation of carbon sources) was monitored by tetrazolium reduction as measured at 590 nm in a spectrophotometric microplate reader.

Bacterial growth was measured every 20 minutes during a total incubation of 18 hours at 32° C. The kinetic data was processed and the background blank values subtracted.

Following completion of the above-referenced Kinetic Growth Assay, the tetrazolium reduction as measured at 590 nm in the microplate is read as an End-Point Kinetic assay. FIG. 4 and FIG. 5 represent histograms of the End-Point Kinetics of the 5937-20° C. *Bacillus coagulans* isolate (GBI-20) and 5937-30° C. *Bacillus coagulans* isolate (GBI-30), respectively.

Biolog™ Analysis of *Bacillus coagulans* Isolates

In order to differentiate the ATCC-type strain *Bacillus coagulans* Hammer (ATCC No. 31284) from the novel strains of *Bacillus coagulans* disclosed herein, the Biolog Microplate System™ was utilized for microbial identification and characterization by carbon source pattern recognition. An innoculum of the ATCC-type strain (ATCC No. 31284) was placed into each of three flasks of Trypticase Soy Broth (TSB). These flasks were then incubated at different temperatures to compensate for any bacterial selection resulting from temperature. After 30 hrs of incubation, an aliquot from each broth flask was aseptically transferred in a laminar flow biological cabinet and plated onto previously prepared and dried TSA medium in Petri plates. Observations for colony forming units (CFU) are made after 24 and 48 hours of incubation at 30° C., 35° C., and 40° C.

The Biolog Microplate System™ was utilized for microbial identification and characterization by carbon source pattern recognition of the *Bacillus coagulans* strains disclosed in the present invention. The aforementioned microplate technique allows for microbial characterization by use of 95 different analytical methods, thus yielding a total of $4 \times 10^{28}$ possible patterns generated from a single microplate. Each strain of microorganism yields a distinct pattern, and the different species of bacteria will give different "families" of patterns which can be recognized and differentiated by the Biolog Microlog™ software. Analytical microplates for the Biolog Microlog™ system are available for gram-negative bacteria, gram-positive bacteria, yeast, lactic acid-producing bacteria, and *E. coli/Salmonella* analysis. In addition, further analyses may also be performed by use of additional selective media.

In brief, characterization of a given microbial isolate is performed by streaking the organism onto a nutrient medium (e.g., GYE or TSA) that will support vigorous microbial proliferation and growth. However, the more fastidious organisms may require chocolate or BIER agar for growth, whereas many "environmental" were found to grow better in the more minimal media. The culture plates were incubated at 28° C. to 35° C. for 4-18 hours.

Following incubation, the bacterial colonies were removed from the culture plate by use of a saline-moistened, cotton swab. A suspension of uniform turbidity was then prepared in 0.85% saline by comparison with a known turbidimetric standard. The bacterial suspension was inoculated into the microplate wells (150 μl/well) and the plate was covered with the associated microplate lid. The covered plates were then incubated at 28° C. to 35° C. for 4 hours or overnight (16-24 hours).

The microplates were then read using a microplate reader at 590 nm. The absorbence or transmittance (i.e., color) in each well was referenced against the negative control well (A-1) so that any purple color recorded above this control level was read as a positive utilization of that particular carbon source. The data were reported as the Percent Color Change as compared to well A-1 utilizing the following formula:

$$\% \text{ Color Change} = \frac{OD_{590}(\text{well})OD_{590}(\text{well } A-1)}{OD_{590}(\text{well } A-1)}$$

Generally, if the Percent Color Change was found to be equal to, or greater than 40, the reaction within the given well was considered to be "positive". However, this value must be empirically determined, as the parameters for each substrate may be different and the positive test below a value of 40 may be possible. The computer algorithms employed provide standardization of settings ensuring repeatability and avoidance of operator bias. Names of all carbon source substrates employed are provided in the results regardless of response.

Table 12, below, illustrates the Total Heterotrophic Plate Count using Trypticase Soy Agar (TSA) for the novel *Bacillus coagulans* strains disclosed herein.

TABLE 12

| DATA: Direct Count, Colony Forming Units (CFU/ml) on TSA | | | |
|---|---|---|---|
| Sample | 24 Hours | 4 Days | Types |
| GBI-1 | $3.00 \times 10^6$ | $2.00 \times 10^7$ | 2 |
| GBI-20 | $<1.00 \times 10^6$ | $5.74 \times 10^6$ | 1 |
| GBI-1 spore shock | $9.30 \times 10^8$ | $4.00 \times 10^9$ | 4 |
| GBI-20 spore shock | $7.20 \times 10^9$ | $7.27 \times 10^9$ | 4 |

Total morphologically different types among samples: 5

Table 13, below, illustrates the approximate percentages of aerobic strain types in each of samples comprising the novel strains of *Bacillus coagulans* disclosed herein.

TABLE 13

| Sample Strain | GBI-1 | GBI-20 | GBI-1 spore shock | GBI-2 spore shock |
|---|---|---|---|---|
| 6022-1 | 50 | | 5 | |
| 6022-2 | 50 | 100 | | 5 |
| 6022-3 | | | 20 | 15 |
| 6022-4 | | | 55 | 60 |
| 6022.5 | | | 20 | 20 |

GC-FAME Processing:

The bacterial strains were streaked onto Trypticase Soy Agar (TSA) plates. The TSA plates were then prepared for Gas Chromatography Fatty Acid Methyl Ester (GC-FAME) analysis following a 24 hour incubation by standard, published GC-FAME methodologies. The bacterial strain was subsequently examined against both the Aerobe (TSBA) and the Clinical Aerobe (CLIN) computer databases. The results of the GC-FAME analysis is shown below, in Table 14.

TABLE 14

| Strain | Primary ID by GC-FAME Aerobic Method | Sim. Coef. | Dist. Coef. |
|---|---|---|---|
| ATCC-99% | Bacillus coagulans | .533 | 3.927 |
| GBI-1 | Bacillus coagulans | .568 | 3.780 |
| GBI-20 | Bacillus coagulans | .542 | 4.176 |
| GBI-30 | Bacillus coagulans | .543 | 3.927 |
| GBI-40 | Bacillus coagulans | .501 | 4.174 |

16S Ribosomal RNA (rRNA) Sequence Analysis
  Materials and Methods
  Sequence analysis of 16S Ribosomal RNA (rRNA) was performed for *Bacillus coagulans* strains: GBI-1; ATCC-99%; GBI-40; GBI-30; and GBI-20.

The protocol used to generate the 16S rRNA gene sequence data is set forth below. The 16S rRNA gene was PCR amplified from genomic DNA isolated from bacterial colonies. The primers which were utilized for the amplification correspond to *E. coli* positions 005 and 531 for the 500 bp package. Excess primers and dNTPs were subsequently removed from the amplification products by use of a Microcon 100™ (Amicon) molecular weight cut-off membranes. The PCR amplification products were then subjected to agarose gel electrophoretic analysis to ascertain both quality and quantity of these products.

Cycle sequencing of the 16S rRNA amplification products was performed using AmpliTaq FS™ DNA polymerase and dRhodamine dye terminators. Excess dye-labeled terminators were removed from the sequencing reactions using a Sephadex G-50 spin column. The amplification products were then collected by centrifugation, dried under vacuum, and stored at −20° C. until use. The products were resuspended in a solution of formamide/blue dextrin/EDTA, and heat-denatured prior to electrophoresis. The samples were electrophoresed on a ABI Prism 377 DNA Sequencer using a pre-poured, 5% Long Ranger™ (RMC) polyacrylamide/urea gel for approximately 6 hours. The resulting sequence data was analyzed using PE/Applied Biosystems DNA editing and assembly software.

The bacterial identifications which were assigned were based upon 16S rRNA gene sequence homology. The sample sequences were identified by comparison against PE Applied Biosystem's MicroSeq™ database utilizing MicroSeq™ sequence analysis software. Sequence alignments which provided the highest degree of sequence homology are presented in a percent genetic distance format (i.e., the percent difference between two aligned sequences). It should be noted that, in this format, a low percentage indicates a high degree of sequence homology. FIG. 6 through FIG. 8 provides alignment of the novel *Bacillus coagulans* strains disclosed in the present invention with various other *Bacillus* species, as well as the results obtained by Neighbor Joining Tree and Concise Alignment analysis. The results for the ATCC-99% isolate are shown in FIG. 6; results for GBI-20 are shown in FIG. 7; and results for GBI-30 are shown in FIG. 8.

Also provided herein are nearest neighbor (see, Saitou and Nei, 1987. *Mol. Biol. Evol.* 4: 406-425) and/or UPGMA (see, Watetnian, 1995. In: *Introduction to Computational Biology*, p. 360-365 (Chapman and Hall Publishing)). Similarly, the "trees" were generated using the alignment sequences matches providing the highest degree of sequence homology.
  Experimental Results
  It should be noted that all experimental results are presented in a genetic distance format, which is essentially the opposite of percent homology.

Species Level: This indicates a species level match. A 16S rRNA sequence homology of greater than 99% is indicative of a species level match (see, Staekebrandt and Goebel, 1994. Taxonomic Note: A Place for DNA-DNA Reassociation and 16S rRNA Sequence Analysis in the Present Species Definition in Bacteriology. *Int. J. Syst. Bacteriol.* 44: 846-849).

Genus Level: This indicates that the sample appears to group within a particular genus but the alignment did not produce a species level match. A genus level match indicates that the sample species is not included in the MicroSeq database.

No Match: This indicates that sample did not group well within any particular genus found in the MicroSeq database. In cases such as this, a search of both the GenBank and Ribosomal Database Project (RDP) databases with the sample sequence was subsequently performed to try to provide a closer match. If the sample sequence does not match well with either of these databases, it may represent a new species or a species whose 16S rRNA gene sequence is not present in any of the databases.

Table 15, below, provides the results of the Percent Genetic Difference studies in tabular form.

TABLE 15

| Strain No. | Identification | % Difference | Confidence Level |
|---|---|---|---|
| GBI-1 | Bacillus coagulans | 1.68% difference | Genus level ID |
| ATCC-99% | Bacillus coagulans | 1.68% difference | Genus level ID |
| GBI-40 | Bacillus coagulans | 1.68% difference | Genus level ID |
| GBI-30 | Bacillus coagulans | 1.68% difference | Genus level ID |
| GBI-20 | Bacillus coagulans | 1.68% difference | Genus level ID |

The 16S rRNA sequence homology was found to be greater than 99% and indicative of a species level match.
Aminopeptidase Profiling
  Aminopeptidase profiling or activity has been used to differentiate bacteria and fungi to species and sub-species (see, e.g., Hughes, et al., 1988. LacZY gene modified peptidase activity in *Pseudomonas aureofaciens*. *Phytopathology* 78: 1502; Hughes, et al., 1989. Identification of immobilized bacteria by aminopeptidase profiling. *Anal. Chem.* 61: 1656-1660), as well as to define ecological niches of parasites and develop media for fastidious organisms. The recent development of a time-resolved, 96-well plate fluorometer provides a rapid and highly sensitive method to obtain peptidase profiles for microbial identification. See, Mossman, et al., 1997. Aminopepetidase profiling using a time-resolved, 96-well plate filter fluorometer. *Appl. Spectroscopy* 51: 1443-1446.

Aminopeptidase profiling was shown to be an effective procedure for the differentiation of the novel strains of *Bacillus coagulans* disclosed herein, from those previously known and characterized (e.g., the ATCC type strain).
Materials and Methods
  The Aminopeptidase profiling analysis disclosed follows the methodologies as set forth by Mossman, et al., 1997. *Appl. Spectroscopy* 51: 1443-1446. Each *Bacillus coagulans* isolate was initially cultured on Tryptic Soy Broth (TSB) Agar plates for 24 hours before washing from the plate with 10 mM, pH 7, phosphate buffer. Table 16, below, illustrates the culture conditions of the various strains of *Bacillus coagulans* which were utilized in the present invention.

TABLE 16

| Ref No. | Strain Name | Growth Temp for Profiling | Comments |
|---|---|---|---|
| Plate 1 | ATCC-99% | 45° C. | 99% majority isolate from ATCC #31284 culture. |
| Plate 2 | GBI-1 | 45° C. | |
| Plate 3 | GBI-30 | 45° C. | Strain grew well at 30° C. |
| Plate 4 | GBI-20 | 45° C. | Strain grown on the bench top at 20° C. |

Following culture, the cell densities were adjusted to 2.5× $10^6$ cells/ml by spectrophotometry at 540 nm (85% transmittance) before placing 0.5 ml into each cell of a 96-well, flat bottom, black, polystyrene plate (FluoroNunc; Nalge-Nunc, Naperville, Ill.). Each well contained one of 20 different non-fluorescent, L-amino acid-β-naphthylamide substrates (Sigma Chemical Co., St. Louis, Mich.) at a final concentration of $1\times10^{-4}$ M. The balance of the microplate well volume of 300 μl consisted of 250 μl of the 10 mM phosphate buffer.

The 20 different peptidase substrates used to produce the profiles included β-naphthylamides of the following amino acids: L-alanine (ALA), L-arginine (ARG), L-asparagine (ASN), L-aspartic acid (ASP), L-cysteine (CYS), glycine (GLY), L-glutamic acid (GLU), L-histidine (HIS), L-isoleucine (I LE), L-leucine (LEU), L-lysine (LYS), DL-methionine (MET), L-phenylalanine (PHE), L-proline (PRO), L-serine (SER), trans hydroxy-L-proline (HPR), L-tryptophan (TRP), L-tyrosine (TYR), and L-valine (VAL). β-naphthylamine, alone, was also used as a positive control. A bacterium blank, substrate blank, and buffer blank were also included in the assay procedure as negative controls. Four replications of each bacterial isolate were run after a 4-hour incubation period.

Aminopeptidase profiles were constructed with data obtained from a time-resolved, laser fluorometric assay of the enzymatically hydrolyzed, fluorescent, β-naphthylamide product from the non-fluorescent, β-naphthylamide substrates. The time-resolved, 96-well plate fluorometer consisted of a sealed tube, nitrogen laser that is guided to a black, flat bottom FluoroNunc 96-well plate via the excitation portion of a bifurcated fiber optic. Fluorescence was collected at a 0° angle to the excitation beam with the emission portion of the bifurcated fiber optic. A 389 nm cut-on filter was used to select the desired emission wavelength before detection with a 931A photomultiplier tube. A total of 25 fluorescent decays were averaged by a Tektronix DSA 602 digital oscilloscope and transferred to a PC computer via an IEEE-488 interface card to provide a readout of relative fluorescence after blank subtraction.

Experimental Results:

Significant differences are detected in the enzyme profile of these *Bacillus coagulans* strains which otherwise are identical for 16S rRNA Sequencing, GC-FAME, and Biolog Identifications. The data is presented for each of the four *Bacillus coagulans* strains in a histogram format plotting fluorescence intensity for each the aminopeptidase enzyme activities listed below. FIG. 9 represents a histogram plot of the of the fluorescence intensity for each the aminopeptidase enzyme activities for the *Bacillus coagulans* 99% ATCC isolate; FIG. 10 represents a histogram plot of the of the fluorescence intensity for each the aminopeptidase enzyme activities for the *Bacillus coagulans* GBI-1 isolate; FIG. 11 represents a histogram plot of the of the fluorescence intensity for each the aminopeptidase enzyme activities for the *Bacillus coagulans* GBI-30 isolate; and FIG. 12 represents a histogram plot of the of the fluorescence intensity for each the aminopeptidase enzyme activities for the *Bacillus coagulans* GBI-20 isolate. Each of the specific Aminopeptidases and controls, as set forth in FIG. 9 through FIG. 12, are identified using numbers 1-24. These numbers are as follows:

| | |
|---|---|
| 1. | L-alanine (ALA) |
| 2. | L-asparagine (ASN) |
| 3. | L-arginine (ARG) |
| 4. | L-aspartic acid (ASP) |
| 5. | L-cysteine (CYS) |
| 6. | L-glutamine (GLN) |
| 7. | L-glutamic acid (GLU) |
| 8. | L-glycine (GLY) |
| 9. | L-histidine (HIS) |
| 10. | L-isoleucine (ILE) |
| 11. | L-leucine (LEU) |
| 12. | L-lysine (LYS) |
| 13. | L-methionine (MET) |
| 14. | L-phenylalanine (PHE) |
| 15. | L-proline (PRO) |
| 16. | trans-hydroxy-L-proline (HPR) |
| 17. | L-serine (SER) |
| 18. | L-threonine (THR) |
| 19. | L-tryptophan (TRP) |
| 20. | L-tyrosine (TYR) |
| 21. | L-valine (VAL) |
| 22. | β-napthylamine (Positive Control) |
| 23. | Buffer (Negative Control) |
| 24. | Buffer with Cells (Negative Control) |

Activity for Numbers 12 (Lysine aminopeptidase) and 22 (β-Napthylamine, 100% control) are not plotted when found to be "off-scale". All cell densities were standardized at 85% T.

The results, illustrated in FIG. 9 through FIG. 12, demonstrate that differences exist in the Aminopeptidase profiles of these *Bacillus coagulans* isolates, despite the overall similarity within the profiles. For example, the 20° C. isolate GBI-20 (see, FIG. 12) is most similar to the 99% isolate (see, FIG. 9) with a dramatic departure in the relative amount of Proline aminopeptidase; whereas the 30° C. isolate GBI-30 (see, FIG. 11) more closely resembles the pattern of the 1% isolate GBI-1 (see, FIG. 10), but departs in the relative amount of Phenylalanine aminopeptidase. Thus, it appears that this methodology may be utilized to both rapidly and effectively differentiate these *Bacillus coagulans* strains.

Use of *Bacillus coagulans* in the Inhibition of Gastrointestinal VRE

The ability of *Bacillus coagulans* vegetative bacteria and spores to inhibit the colonization of Vancomycin-Resistant Enterococci (VRE) was examined. Prior to the disclosure of the present invention, no effective therapy was available to decrease either the amount or the duration of intestinal colonization with VRE. For example, many antibiotics have been shown to have only a very transient effect on VRE colonization. Thus, the development of a safe and efficacious therapeutic for the amelioration of VRE colonization would serve to significantly reduce the potentially fatal consequences of VRE infection, the transmission of VRE between patients hospital costs, and patient and healthcare-provider inconvenience.

Materials and Methods

A murine model, initially developed to study the effect of various antibiotics on persistence of VRE intestinal colonization, was used in these experiments. Two sets of experiments, using a total of 33 mice were performed. High-level VRE colonization was established in all 33 mice by administering approximately $5 \times 10^8$ VRE by oral gavage, while concurrently administering subcutaneous Clindamycin daily for 5 days. This method consistently results in development of high levels of VRE fecal colonization in mice (mean=9 $\log_{10}$ CFU/gram of stool).

The mice were then divided into 3 experimental groups and the following agents were administered: Group 1=saline by oral gavage for 4 days (11 total control mice); Group 2=*Bacillus coagulans* overnight culture approximately $1 \times 10^7$ vegetative organisms by oral gavage for 4 days (17 total mice); and Group 3=*Bacillus coagulans* spores approximately $1 \times 10^7$ organisms by oral gavage for 4 days (5 total mice). Stool samples were collected at 3 to 5 day intervals during the experiment to determine the levels of VRE and *Bacillus coagulans*. Stool samples were homogenized, serially diluted in saline, and plated on enterococcosel-selective agar for quantification of VRE, or on BHI agar containing 6 μg/ml of aztreonam and 6 μg/ml of Nystatin for quantification of *Bacillus coagulans*. If VRE were not detectable in a sample, the lower limit of detection was assigned.

Preliminary Microbiology Results

Kirby-Bauer Antibiotic Susceptibility Testing:

| | |
|---|---|
| Susceptible to: | ampicillin, ciprofloxacin, trimethoprim-sulfamethoxazole, rifampin, erythromycin, vancomycin, gentamicin, and oxacillin |
| Intermediate Susceptibility to: | tetracycline |

Vitek Machine-Based Susceptibility Testing:

| | |
|---|---|
| Susceptible to: | penicillin, vancomycin, gentamicin (500 μg/ml), streptomycin(2,000 μg/ml), nitrofurantoin, norfloxacin, and chloramphenicol |
| Resistant to: | tetracycline |

Nitrocefin Testing:

Positive low-level β-lactamase production

Murine Conolization

*Bacillus coagulans* was given to eight mice to determine the doses to be used in the subsequent, formal experiments. All mice were colonized with high levels of VRE (>9 $\log_{10}$ CFU/gram of stool) prior to administration of *Bacillus coagulans*. Control mice received no treatment. *Bacillus coagulans* was administered daily by gastric gavage in three different doses: $1.5 \times 10^6$ CFU/kg=usual human dose, $2.5 \times 10^8$ CFU/kg and $3.5 \times 10^9$ CFU/kg. The level of VRE in stool was determined after 5 days. The results of these preliminary studies are shown below in Table 17.

TABLE 17

| Treatment | Mice Group No. | Mean Level of VRE on Day 5 |
|---|---|---|
| Control mice (no treatment) | 4 | 6.6 $\log_{10}$CFU/g stool |
| $5 \times 10^6$ CFU/kg/day | 4 | 6.0 $\log_{10}$CFU/g stool |
| $5 \times 10^8$ CFU/kg/day | 3 | *3.5 $\log_{10}$CFU/g stool |
| $5 \times 10^9$ CFU/kg/day | 1 | 3.7 $\log_{10}$CFU/g stool |

*The level of VRE was below the level of detection (<=1.7 $\log_{10}$CFU/g) for 2/3 mice treated with $5 \times 10^8$ CFU *Bacillus coagulans*/kg/day. The lower limit of detection was assigned to these mice.

By use of the aforementioned colonization methodology, high-levels of VRE colonization was initially established in all of the mice (i.e., 7.1 to 10.2 $\log_{10}$ VRE/gram of stool). The initial level of VRE present in the saline control mice and the *Bacillus coagulans* mice was not significantly different. The level of VRE declined gradually in all of the saline control mice after Clindamycin was discontinued (consistent with previous experiments).

In comparison to the saline controls, the level of VRE declined more rapidly in the mice receiving *Bacillus coagulans*. Five days after clindamcin was discontinued (after 4 days of *Bacillus coagulans* therapy), the mean level of VRE was found to be 5.3 $\log_{10}$ VRE/gram of stool compared with 6.7 $\log_{10}$ VRE/gram of stool in the saline controls. This represented a 25-fold reduction in VRE levels (p<0.05). Eight days after clindamycin was discontinued (4 days after *Bacillus coagulans* therapy was completed), the mean level of VRE was found to be 2.9 $\log_{10}$ VRE/gram of stool compared with 4.3 $\log_{10}$ VRE/gram of stool in the saline controls. This represented a 28-fold reduction (p<0.05). Thirty-five percent (6/17 animals) of *Bacillus coagulans* treated mice had undetectable levels of VRE eight days after clindamycin was discontinued, whereas none of the saline controls had undetectable levels of VRE at that time point (p<0.05). The mean level of VRE present in the stool of the 5 mice receiving *Bacillus coagulans* spores was also significantly lower than the level in the saline control mice (p<0.05), however none of these five mice had undetectable VRE levels.

All of the mice receiving *Bacillus coagulans* had detectable levels of *Bacillus coagulans* in their stool one day after completion of four days of therapy (range 3.1 to 6.4 $\log_{10}$ CFU/gram of stool) and all of these mice still had low levels of *Bacillus coagulans* detectable in their stool 4 days after completion of therapy.

These studies demonstrated that the oral administration of *Bacillus coagulans* (in the form of both vegetative bacteria and spores) resulted in a significant decrease in the level of VRE in the stool of colonized mice, in comparison with saline controls. The results which were obtained with the use of this murine model correlate well with the findings in various studies which were examined VRE-colonized human patients. Therefore, this established mouse model provides a means to study the efficacy of agents designed to eliminate VRE colonization. Thirty-five percent of mice receiving *Bacillus coagulans* were found to have undetectable levels of VRE four days after completing therapy. In comparison, none of the mice receiving saline were VRE-free. On average, a 25- to 28-fold reduction in the level of VRE was observed in the *Bacillus coagulans*-treated mice in comparison with the saline-treated mice. Moreover, sixty-five percent of mice receiving *Bacillus coagulans* had a reduction of VRE equal to approximately 50-times the original inoculation. Therefore, all of the test mice had a significant VRE load reduction, with 60% of the mice exhibiting a 2-log VRE diminution and 40% with complete eradication of Enterococci with statistical zero percent recovery of VRE in the mouse stool. These results suggest that *Bacillus coagulans* therapy is an effective means to ameliorate both the level and duration of VRE colonization in human patients.

The inhibition of VRE by *Bacillus coagulans* does not appear to involve any of the mechanisms of inhibition traditionally though to be used by probiotic bacteria such as *Bacillus coagulans*. As previously discussed, there are two primary mechanisms used by acid-producing *Bacillus* for elimination of microbes. These mechanisms are:

Competitive Inhibition or Exclusion: Which is the ability of most Bacillicea to out-compete other organisms for substrate and trace minerals. This usually involves the mass proliferation of the *Bacillus*.

Micro-Environment Modification: Which usually serves to alter the physiological or biochemical properties or activities of bacteria's cell membrane by the production of acid (e.g., lactic, acetic, etc.) or other agents possessing anti-microbial properties.

Although there was a dramatic decrease in the VRE levels (i.e., 2-logs in the 60% effective group and 40% in the total eradication group), the results show that there was no corresponding increase in *Bacillus coagulans* concentrations of the treated groups (expressed in CFU per gram of mouse stool). It appears that one experimental group showed substantially better results than another successful group, but without a corresponding *Bacillus* enumeration to justify it. Accordingly, these results suggest that Competitive Inhibition by the *Bacillus coagulans* is not the mechanism which gave rise to the mitigation of VRE levels in this study.

Additionally, it is also known that Enterococci are not inhibited by changes in the pH of its micro-environment. For example, *Enterococcus faecium* (which is the *Enterococcus* species responsible for most, if not all, VRE carriage and infections) is used as a probiotic in the animal production industry. This organism, itself, produces a D-optical isomer of lactic acid and is generally co-administered with *Lactobacillus* and *Bifidiobacterium*, which produce the L-optical isomer of lactic acid. Therefore, *Enterococcus faecium* is not affected by lactic acid-producing organisms, regardless of optical isomer of lactic acid produced. Accordingly, the second method used by probiotic bacteria (micro-environmental changes) to inhibit microbial colonization, does not appear to play a role in the inhibition of VRE by *Bacillus coagulans*. Due to the aforementioned experimental results, it is believed that the amelioration of VRE by *Bacillus coagulans* is due to the production of one or more anti-microbial agents by the *Bacillus*. This anti-microbial agent may be an organic molecule(s) and/or an thermo-tolerant protein(s).

A composition for inhibiting VRE growth contains a large concentration (i.e., $1\times10^9$ to $1\times10^{11}$ CFU) of *Bacillus coagulans* vegetative bacteria and/or spores in combination with the culture medium (supernatant) in either an unpurified or semi-purified form. As with *Bacillus coagulans* vegetative cells and spores, the culture medium has also been designated a GRAS classification by the FDA. In order to reduce the overall volume, the medium may be partially- or fully lyophilized. Thus, the concomitant administration of both the vegetative bacteria/spores and a supernatant component of some type would serve to ensure that all possible probiotic inhibitory mechanisms (i.e., antibiosis, parasitism, competitive inhibition and microenvironment/pH modification) were covered by the administration of the aforementioned therapeutic composition.

As previously discussed supra, *Bacillus coagulans* culture medium has been shown to contain extracellular product(s), produced and secreted by the bacteria, which possess marked anti-microbial properties against bacteria, fungus, yeast, and virus. Methodologies for the purification of the one or more agents responsible for these anti-microbial properties are also currently under development. A preferred embodiment of the present invention would, accordingly, comprise a large concentration (i.e., $1\times10^9$ to $1\times10^{11}$ CFU) of *Bacillus coagulans* vegetative bacteria and/or spores in combination with the either a purified or semi-purified form of these extracellular product(s).

*Bacillus coagulans* therapy is also useful to inhibit other strains of VRE. Similarly, the *Bacillus coagulans* is used to prevent or ameliorate the level of colonization of other pathogenic organisms such as *Candida* species, *Salmonella*, coagulase-negative *Staphylococci*, and multi-resistant gram-negative rods such as *Klebsiella* species and *Escherichia coli*.

EQUIVALENTS

From the foregoing detailed description of the specific embodiments of the present invention, it should be readily apparent that a unique methodology for the utilization of lactic acid-producing bacteria, preferably *Bacillus coagulans*, for the prevention and treatment of gastrointestinal tract pathogens and their associated diseases, has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular antibiotic which is utilized in the Therapeutic Composition of the present invention is believed to be a matter of routine for a person of ordinary skill in the art with knowledge of the embodiments described herein.

Other embodiments are within the following claims.

We claim:

1. A method of maintaining gastrointestinal tract health comprising administering to the gastrointestinal tract of a mammal a composition comprising an isolated *Bacillus coagulans* GBI-30 strain (ATCC Designation Number PTA-6086), wherein said strain colonizes the gastrointestinal tract of said mammal to maintain gastrointestinal health.

2. The method of claim 1, wherein said composition is administered orally, buccally, or nasally.

3. The method of claim 1, wherein said composition is administered in a food or as a food supplement.

4. The method of claim 1, wherein said strain produces lactic acid and has an optimal growth temperature of in the range of 25-35° C.

5. The method of claim 1, wherein said strain produces lactic acid and has an optimal growth temperature of 30° C.

6. The method of claim 1, wherein said strain produces L(+) dextrorotatory lactic acid and produces spores resistant to temperatures of up to approximately 90° C.

7. The method of claim 1, wherein said composition comprises a viable *Bacillus coagulans* GBI-30 strain (ATCC Designation Number PTA-6086) vegetative bacterial cell.

8. The method of claim 1, wherein said composition comprises a viable *Bacillus coagulans* GBI-30 strain (ATCC Designation Number PTA-6086) bacterial spore.

9. The method of claim 1, wherein said composition comprises $1\times10^3$ to $1\times10^{14}$ CFU of *Bacillus coagulans* GBI-30 strain (ATCC Designation Number PTA-6086).

10. The method of claim 1, wherein said composition comprises $1\times10^8$ to $1\times10^{10}$ CFU of *Bacillus coagulans* GBI-30 strain (ATCC Designation Number PTA-6086).

11. The method of claim 1, wherein said composition comprises $1\times10^9$ CFU of *Bacillus coagulans* GBI-30 strain (ATCC Designation Number PTA-6086).

* * * * *